United States Patent [19]

White et al.

[11] Patent Number: 5,281,703

[45] Date of Patent: Jan. 25, 1994

[54] PROCESS FOR MAKING ANTIMICROBIAL QUINOLONYL LACTAMS

[75] Inventors: Ronald E. White; Thomas P. Demuth, Jr., both of Norwich, N.Y.

[73] Assignee: Procter & Gamble Pharmaceuticals, Inc., Norwich, N.Y.

[21] Appl. No.: 59,529

[22] Filed: May 7, 1993

Related U.S. Application Data

[63] Continuation of Ser. No. 769,615, Oct. 1, 1991, abandoned.

[51] Int. Cl.$^5$ ................ C07D 499/04; C07D 499/08; C07D 499/12; C07D 205/12
[52] U.S. Cl. .................................. 540/302; 540/201; 540/215; 540/217; 540/219; 540/222; 540/223; 540/224; 540/225; 540/316; 540/304; 540/310; 540/312; 540/313; 540/314; 540/315; 540/317; 540/346
[58] Field of Search ............... 540/201, 215, 217, 219, 540/222, 223, 224, 225, 302, 304, 310, 312, 313, 314, 315, 316, 317, 346

[56] References Cited

FOREIGN PATENT DOCUMENTS

| | | |
|---|---|---|
| 87/75009 | 1/1988 | Australia . |
| 88/27554 | 6/1989 | Australia . |
| 335297 | 10/1989 | European Pat. Off. . |
| 366189 | 5/1990 | European Pat. Off. . |
| 366193 | 5/1990 | European Pat. Off. . |
| 366640 | 5/1990 | European Pat. Off. . |
| 366641 | 5/1990 | European Pat. Off. . |
| 0451764A1 | 10/1991 | European Pat. Off. . |
| WO91/16327 | 10/1991 | World Int. Prop. O. . |

OTHER PUBLICATIONS

Sandler & Kairo, "O-Carbamates", *Organic Functional Group Preparations*, vol. II, Chap. 11, pp. 235-242, 1971.
S. Kukolja et al., "Oral Absorption of Cephalosporin Antibiotics, 1. Synthesis, Biological Properties, and Oral Bioavailability of 7-(Arylacetamido)-3-chloro Cephalosporins in Animals", *J. Med. Chem.* vol. 31, pp. 1987-1993, 1988.
S. Schmitt et al., "The Synthesis of 2-(Functionalized Methyl)-1β-Methyl-Carbapenems", *J. Antibiotics*, vol. 41, p. 780, 1988.

(List continued on next page.)

*Primary Examiner*—Johann Richter
*Attorney, Agent, or Firm*—David L. Suter; Jacobus C. Rasser

[57] ABSTRACT

The present invention provides methods of making compounds of the structure $$[Q-L^1]-L-[L^2-B[$$

wherein
 (I) Q is a quinolone moiety;
 (II) B is a beta-lactam moiety;
 (III) L, $L^1$, and $L^2$ together comprise a carbamate-containing linking moiety comprising the steps of:
 (1) Reacting a lactam compound of the formula B-$L^4$-H with phosgene to form an intermediate compound of the formula B—$L^4$—C(=O)—Cl, where $L^4$ is oxygen; and
 (2) Coupling said intermediate compound with a quinolone compound of the formula Q-$L^3$-$R^{44}$; wherein $L^3$ is nitrogen; $R^{44}$ is hydrogen, Si($R^{45}$)$_3$, or Sn($R^{45}$)$_3$; and $R^{45}$ is lower alkyl.

Preferably, the process additionally comprises steps prior to the reacting and coupling steps where esters of the lactam and quinolone compounds are made. Also preferably, the coupling step comprises adding a solution containing the quinolone compound to a solution containing the intermediate compound. The process steps are also preferably performed at a temperature of from about −80° C. to about 0° C. Preferred antimicrobial compounds made by these processes are those where the beta-lactam moiety is a penem.

17 Claims, No Drawings

OTHER PUBLICATIONS

D. G. Walker et al., "Use of Bistrimethylsilylated Intermediates in the Preparation of Semisynthetic 7-Amino-3-substituted-cephems. Expedient Syntheses of a new 3-[1-Methyl-1-pyrrolidinio)methyl]cephalosporin", *J. Org. Chem.*, vol. 53, pp. 983–991, 1988.

M. Alpegiani et al., "2-(Heteroatom-substituted)-Methyl Penems. IV. Oxygen Derivatives", *Heterocycles*, vol. 30, No. 2, pp. 799–812, 1990.

A. J. Corraz et al., "Dual-Action' Penems", Abstract-825, 31st *Interscience Conference on Antibacterial Agents and Chemotherapy*, Oct. 1, 1991.

A. J. Corraz et al., "Dual-Action' Penems and Carbapenems", Abstract-826, 31st *Interscience Confernce on Antibacterial Agents and Chemotherapy*, Oct. 1, 1991.

A. J. Corraz et al., Handout distributed at poster presentation, 31st Interscience Conference on Antibacterial Agents and Chemotherapy, Oct. 1, 1991.

A. J. Corraz et al., "Dual-Action Penems and Carbapenems", *J. Med. Chem.*, vol. 35, pp. 1828–1839, 1992.

PROCESS FOR MAKING ANTIMICROBIAL QUINOLONYL LACTAMS

This is a continuation of application Ser. No. 07/769,615, filed on Oct. 1, 1991, now abandoned.

BACKGROUND OF THE INVENTION

This invention relates to processes for making antimicrobial compounds. The compounds made by this invention contain, as integral substituents, a quinolone moiety and a lactam-containing moiety.

The chemical and medical literature describes a myriad of compounds that are said to be antimicrobial, i.e., capable of destroying or suppressing the growth or reproduction of microorganisms, such as bacteria. In particular, antibacterials include a large variety of naturally-occurring (antibiotic), synthetic, or semi-synthetic compounds. They may be classified (for example) as the aminoglycosides, ansamacrolides, beta-lactams (including penicillins and cephalosporins), lincosaminides, macrolides, nitrofurans, nucleosides, oligosaccharides, peptides and polypeptides, phenazines, polyenes, polyethers, quinolones, tetracyclines, and sulfonamides. Such antibacterials and other antimicrobials are described in *Antibiotics, Chemotherapeutics, and Antibacterial Agents for Disease Control* (M. Grayson, editor, 1982), and E. Gale et al., *The Molecular Basis of Antibiotic Action* 2d edition (1981), both incorporated by reference herein.

Recently, a new class of highly potent, broad spectrum antimicrobials was discovered, combining beta-lactam moieties with quinolone moieties. These compounds have been referred to as "Quinolonyl Lactam Antimicrobials" (herein referred to as "QLAs"). Such compounds are described in European Patent Publication 366,189, White and Demuth, published May 2, 1990; European Patent Publication 366,193, Demuth and White, published May 2, 1990; European Patent Publication 366,640, Demuth and White, published May 2, 1990; and European Patent Publication 366, 641, White and Demuth, published May 2, 1990. Other such compounds are described in Australian Patent Publication 87/75009, Albrecht et al., published Jan. 7, 1988; Australian Patent Publication 88/27554, published Jun. 6, 1989; European Patent Publication 335, 297, Albrecht et al., published Oct. 4, 1989; and Albrecht et al., "Dual-Action Cephalosporing: Cephalosporin 3'-Quinolone Carbamates", 34 *J. Medicinal Chemistry* 2857 (1991).

Manufacture of QLAs generally involves synthesis of suitably protected substituent beta-lactam and quinolone moieties, a linking process, and appropriate de-protection steps. The specific linking process depends, of course, on the specific lactam and quinolone substituent moieties used, as well as the type of linkage desired. Several such linking processes have been described in the literature. However, the yields of these processes are often low, particularly for the preparation of QLAs having a penem substituent moiety.

It has now been discovered that certain linking processes using phosgene are useful in making QLAS, particularly those having a penem substituent moiety. Such processes allow efficient synthesis of QLAS, with high yields.

SUMMARY OF THE INVENTION

The present invention provides methods of making compounds of the structure $[Q-L^1]-L-[L^2-B]$ wherein (I) Q is a structure according to Formula (I)

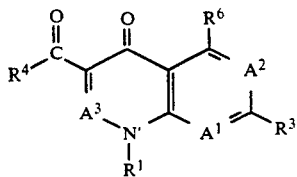

wherein (A) (1) $A^1$ is N or $C(R^7)$; where
  (i) $R^7$ is hydrogen, hydroxy, alkoxy, nitro, cyano, halogen, alkyl, or $N(R^8)(R^9)$, and
  (ii) $R^8$ and $R^9$ are, independently, $R^{8a}$ where $R^{8a}$ is hydrogen, alkyl, alkenyl, carbocyclic ring, or heterocyclic ring; or $R^8$ and $R^9$ together comprise a heterocyclic ring including the nitrogen to which they are bonded;
(2) $A^2$ is N or $C(R^2)$; where $R^2$ is hydrogen or halogen;
(3) $A^3$ is N or $C(R^5)$; where $R^5$ is hydrogen;
(4) $R^1$ is hydrogen, alkyl, a carbocyclic ring, a heterocyclic ring, alkoxy, hydroxy, alkenyl, arylalkyl, or $N(R^8)(R^9)$;
(5) $R^3$ is hydrogen, halogen, alkyl, a carbocyclic ring, or a heterocyclic ring;
(6) $R^4$ is hydroxy; and
(7) $R^6$ is hydrogen, halogen, nitro or $N(R^8)(R^9)$;
(B) except that
(1) when $A^1$ is $C(R^7)$, $R^1$ and $R^7$ may together comprise a heterocyclic ring including N' and $A^1$;
(2) when $A^2$ is $C(R^2)$, $R^2$ and $R^3$ may together comprise $-O-(CH_2)_n-O-$, where n is an integer from 1 to 4;
(3) when $A^3$ is $C(R^5)$, $R^4$ and $R^5$ may together comprise a heterocyclic ring including the carbon atoms to which $R^4$ and $R^5$ are bonded and the carbon atom of Formula (I) to which said carbon atoms are bonded; and
(4) when $A^3$ is $C(R^5)$, $R^1$ and $R^5$ may together comprise a heterocyclic ring including N' and the adjacent carbon to which $R^5$ is bonded;
(C) and except that one of $R^1$, $R^6$, or $R^3$ must be nil;
(II) B is a structure according to Formula (II):

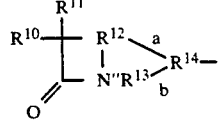

wherein
(A) $R^{10}$ is hydrogen, halogen, alkyl, alkenyl, heteroalkyl, a carbocyclic ring, a heterocyclic ring, $R^{8a}-O-$, $R^{8a}CH=N-$, $(R^8)(R^9)N-$, $R^{17}-C(=CHR^{20})-C(=O)NH-$, $R^{17}-C(=NO-R^{19})-C(=O)NH-$, or $R^{18}-(CH_2)_m-C(=O)NH-$; where
(1) m is an integer from 0 to 9;

(2) $R^{17}$ is hydrogen, alkyl, alkenyl, heteroalkyl, heteroalkenyl, a carbocyclic ring, or a heterocyclic ring;

(3) $R^{18}$ is $R^{17}$, $-Y^1$, or $-CH(Y^2)(R^{17})$;

(4) $R^{19}$ is $R^{17}$, arylalkyl, heteroarylalkyl, $-C(R^{22})(R^{23})COOH$, $-C(=O)O-R^{17}$, or $-C(=O)NH-R^{17}$, where $R^{22}$ and $R^{23}$ are, independently, $R^{17}$ or together comprise a carbocyclic ring or a heterocyclic ring including the carbon atom to which $R^{22}$ and $R^{23}$ are bonded;

(5) $R^{20}$ is $R^{19}$, halogen, $-Y^1$, or $-CH(Y^2)(R^{17})$;

(6) $Y^1$ is $-C(=O)OR^{21}$, $-C(=O)R^{21}$, $-N(R^{24})R^{21}$, $-S(O)_pR^{29}$, or $-OR^{29}$; and $Y^2$ is $Y^1$ or $-OH$, $-SH$, or $-SO_3H$;

(a) p is an integer from 0 to 2;

(b) $R^{24}$ is hydrogen; alkyl; alkenyl; heteroalkyl; heteroalkenyl; a carbocyclic ring; a heterocyclic ring; $-SO_3H$; $-C(=O)R^{25}$; or, when $R^{18}$ is $-CH(N(R^{24})R^{21})(R^{17})$, $R^{24}$ may comprise a moiety bonded to $R^{21}$ to form a heterocyclic ring; and (c) $R^{25}$ is $R^{17}$, $NH(R^{17})$, $N(R^{17})(R^{26})$, $O(R^{26})$, or $S(R^{26})$; where $R^{26}$ is alkyl, alkenyl, a carbocyclic ring, a heterocyclic ring, or when $R^{25}$ is $N(R^{17})(R^{26})$, $R^{26}$ may be a moiety bonded to $R^{17}$ to form a heterocyclic ring; and (7) $R^{21}$ is $R^{29}$ or hydrogen; where $R^{29}$ is alkyl; alkenyl; arylalkyl; heteroalkyl; heteroalkenyl; heteroarylalkyl; a carbocyclic ring; a heterocyclic ring; or, when Y is $N(R^{24})R^{21}$ and $R^{21}$ is $R^{29}$, $R^{21}$ and $R^{24}$ may together comprise a heterocyclic ring including the nitrogen atom to which $R^{24}$ is bonded;

(B) $R^{11}$ is hydrogen, halogen, alkoxy, or $R^{27}C(=O)NH-$, where $R^{27}$ is hydrogen or alkyl;

(C) bond "a" is a single bond or is nil; and bond "b" is a single bond, a double bond, or is nil; except bond "a" and bond "b" are not both nil;

(D) $R^{12}$ is $-C(R^{8a})-$, or $-CH_2-R^{28}-$; where $R^{28}$ is $-C(R^{8a})$, $-O-$, or $-N-$, and $R^{28}$ is directly bonded to N" in Formula (II) to form a 5-membered ring; except, if bond "a" is nil, then $R^{12}$ is (1) $-C(R^{8a})(X^1)-$, where (i) $X^1$ is $-R^{21}$; $-OR^{30}$; $-S(O)_rR^{30}$, where r is an integer from 0 to 2; $-OC=O)R^{30}$; or $N(R^{30})R^{31}$; and (ii) $R^{30}$ and $R^{31}$ are, independently, alkyl, alkenyl, carbocyclic ring or heterocyclic ring substituents; or $R^{30}$ and $R^{31}$ together comprise a heterocyclic ring including the nitrogen atom to which $R^{30}$ and $R^{31}$ are bonded; or (2) $-CH_2-R^{32}-$; where $R^{32}$ is $-C(R^{8a})(R^{21})$, $-O-$, or $-NR^{8a}$, and $R^{32}$ is directly bonded to N" in Formula (II) to form a 5-membered ring;

(E) (1) if bond "b" is a single bond, $R^{13}$ is $-CH(R^{33})-$; or, $-C(O)NHSO_2-$, if bond "a" is nil; or $-C^*(R^{33})-$ if $R^{14}$ contains a $R^{36}$ moiety; where $R^{33}$ is hydrogen or COOH, and $C^*$ is linked to $R^{36}$ to form a 3-membered ring;

(2) if bond "b" is a double bond, $R^{13}$ is $-C(R^{33})=$; or (3) if bond "b" is nil, $R^{13}$ is hydrogen, $-SO_3H$, $-PO(OR^{34})OH$, $-C(O)NHSO_2N(R^{34})(R^{35})$, $-OSO_3H$, $-CH(R^{35})COOH$, or $-OCH(R^{34})COOH$; where $R^{34}$ is hydrogen, alkyl, alkenyl, a carbocyclic ring, or a heterocyclic ring; and $R^{35}$ is hydrogen, alkyl, alkenyl, or $-NHR^{8a}$; or, if $R^{13}$ is $-C(O)NHSO_2N(R^{34})(R^{35})$, $R^{34}$ and $R^{35}$ may together comprise a heterocyclic ring including the nitrogen to which $R^{34}$ and $R^{35}$ are bonded; and (F) (1) if bond "a" or bond "b" is nil, then $R^{14}$ is nil;

(2) if bond "a" and "b" are single bonds, $R^{14}$ is $-W-C'''=C(R^{8a})-R^{37}-$, or $-W-C'''(R^{36})-R^{37}-$; or (3) if bond "a" is a single bond and bond "b" is a double bond, $R^{14}$ is $-C(R^{8a})(R^{38})-W-C'''-R^{37}-$; $-W'-C(R^{8a})(R^{38})-C'''-R^{37}-$; or $-W-C'''-R^{37}-$; where (a) W is O; $S(O)_s$, where s is an integer from 0 to 2; or $C(R^{38})$, where $R^{38}$ is hydrogen, alkyl or alkoxy;

(b) W' is O; or $C(R^{38})$;

(c) $R^{36}$ hydrogen; alkyl; alkenyl; $-COOH$; or, if $R^{13}$ is $-C^*(R^{33})$, $R^{36}$ may be linked to $C^*$ to form a 3-membered carbocyclic ring;

(d) $R^{37}$ and is nil, alkyl, alkenyl, a carbocyclic ring, or a heterocyclic ring; and (e) C''' is directly bonded to $R^{13}$ to form a 5- or 6-membered ring; and (III)(A) L is $-C(=O)-$, and is bonded to $L^3$ and $L^4$ (B) $L^1$ is $L^3$ or $R^{15}L^3$; where (1) $L^3$ is nitrogen;

(2) $R^{15}$ is alkyl, alkenyl, heteroalkyl, a heterocyclic ring, a carbocyclic ring, or $R^{15}$ together with $L^3$ is a heteroalkyl or a heterocyclic ring; and (3) $L^1$ is bonded to Q at the point of attachment of $R^1$, $R^6$ or $R^3$, whichever is nil;

(C) $L^2$ is $L^4$, $-X^2-R^{39}-L^4$, or $-X^3-R^{39}-L^4$; where (1) $L^4$ is oxygen;

(2) $X^2$ is oxygen, or $S(O)_v$, where v is 0, 1, or 2;

(3) $X^3$ is nitrogen; $N(R^{40})$; $N^+(R^{41})(R^{42})$; or $R^{43}-N(R^{41})$; and is linked to $R^{14}$ by a single or double bond; or, if $R^{14}$ is nil, $X^3$ is linked to B by a single or double bond; where (a) $R^{40}$ is $R^{8a}$; $-OR^{8a}$; or $-C(=O)R^{8a}$;

(b) $R^{41}$ and $R^{42}$ are, independently, hydrogen; alkyl; alkenyl; carbocyclic rings; heterocyclic rings; or, if $R^6$ is $R^{16}X$, then $R^{41}$ and $R^{42}$ together with Q" may comprise a heterocyclic ring as $R^{16}$;

(c) $R^{43}$ is $N(R^{41})$, oxygen or sulfur;

(4) t is 0 or 1;

(5) $R^{39}$ is alkyl, alkenyl, heteroalkyl, heteroalkenyl, a carbocyclic ring, or a heterocyclic ring; and (6) (a) if bond "a" or bond "b" is nil, then $L^2$ is bonded directly to $R^{12}$ or $R^{13}$; or (b) if bond "a" and bond "b" are not nil, then $L^2$ is bonded to $R^{14}$;

and pharmaceutically-acceptable salts and biohydrolyzable esters thereof, and hydrates thereof;

comprising the steps of:

(1) Reacting a lactam compound of the formula $B-L^4-H$ with phosgene to form an intermediate compound of the formula $B-L^4-C(=O)-Cl$; and (2) Coupling said intermediate compound with a quinolone compound of the formula $Q-L^3-R^{44}$; wherein $R^{44}$ is hydrogen, $Si(R^{45})_3$, or $Sn(R^{45})_3$; and $R^{45}$ is lower alkyl.

Preferably, the process additionally comprises steps prior to the reacting and coupling steps where esters of the lactam and quinolone compounds are made. Also preferably, the coupling step comprises adding a solution containing the quinolone compound to a solution containing the intermediate compound. The process steps are also preferably performed at a temperature of from about −80° C. to about 0° C. Preferred antimicrobial compounds made by these processes are those where $R^{14}$ is $-W-C'''-R^{37}-$, more preferably wherein W is $S(O)_s$.

DESCRIPTION OF THE INVENTION

The present invention encompasses methods for making certain QLAs. These compounds are useful for treating infectious disorders in humans or other animal subjects. Thus, the compounds made by this invention must be pharmaceutically acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio.

OLAs

The compounds ("QLAs") made by the methods of this invention encompass any of a variety of lactam moieties linked, by a linking moiety, to a quinolone moiety at the 1-, 5-, or 7-position of the quinolone. These compounds include those having the general formula

[Q-L¹]-L-[L²-B]

wherein (I) Q is a structure according to Formula (I)

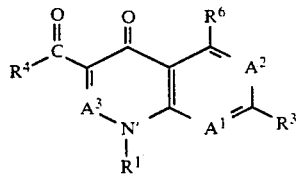

(I)

wherein (A) (1) $A^1$ is N or $C(R^7)$; where
   (i) $R^7$ is hydrogen, hydroxy, alkoxy, nitro, cyano, halogen, alkyl, or $N(R^8)(R^9)$ (preferably hydrogen or halogen), and
   (ii) $R^8$ and $R^9$ are, independently, $R^{8a}$ where $R^{8a}$ is hydrogen, alkyl, alkenyl, carbocyclic ring, or heterocyclic ring; or $R^8$ and $R^9$ together comprise a heterocyclic ring including the nitrogen to which they are bonded;
(2) $A^2$ is N or (preferably) $C(R^2)$; where $R^2$ is hydrogen or halogen;
(3) $A^3$ is N or (preferably) $C(R^5)$; where $R^5$ is hydrogen;
(4) $R^1$ is hydrogen, alkyl, a carbocyclic ring, a heterocyclic ring, alkoxy, hydroxy, alkenyl, arylalkyl, or $N(R^8)(R^9)$ (preferably alkyl or a carbocyclic ring);
(5) $R^3$ is hydrogen, halogen, alkyl, a carbocyclic ring, or a heterocyclic ring (preferably a heterocyclic ring);
(6) $R^4$ is hydroxy; and
(7) $R^6$ is hydrogen, halogen, nitro or $N(R^8)(R^9)$;
(B) except that
   (1) when $A^1$ is $C(R^7)$, $R^1$ and $R^7$ may together comprise a heterocyclic ring including N' and $A^1$;

(2) when $A^2$ is $C(R^2)$, $R^2$ and $R^3$ may together comprise $-O-(CH_2)_n-O-$, where n is an integer from 1 to 4;
(3) when $A^3$ is $C(R^5)$, $R^4$ and $R^5$ may together comprise a heterocyclic ring including the carbon atoms to which $R^4$ and $R^5$ are bonded and the carbon atom of Formula (I) to which said carbon atoms are bonded; and
(4) when $A^3$ is $C(R^5)$, $R^1$ and $R^5$ may together comprise a heterocyclic ring including N' and the adjacent carbon to which $R^5$ is bonded;
(C) and except that one of $R^1$, $R^6$, or $R^3$ must be nil;
(II) B is a structure according to Formula (II):

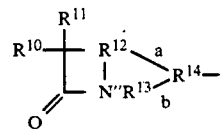

(II)

wherein
(A) $R^{10}$ is hydrogen, halogen, heteroalkyl, a carbocyclic ring, a heterocyclic ring, $R^{8a}-O-$, $R^{8a}CH=N-$, $(R^8)(R^9)N-$, $R^{17}-C(=CHR^{20})-C(=O)NH-$, or (preferably) alkyl, alkenyl, $R^{17}-C(=NO-R^{19})-C(=O)NH-$, or $R^{18}-(CH_2)_m-C(=O)NH-$; where
   (1) m is an integer from 0 to 9 (preferably from 0 to 3);
   (2) $R^{17}$ is hydrogen, alkyl, alkenyl, heteroalkyl, heteroalkenyl, a carbocyclic ring, or a heterocyclic ring (preferably alkyl, a carbocyclic ring, or a heterocyclic ring);
   (3) $R^{18}$ is $R^{17}$, $-Y^1$, or $-CH(Y^2)(R^{17})$;
   (4) $R^{19}$ is $R^{17}$, arylalkyl, heteroarylalkyl, $-C(R^{22})(R^{23})COOH$, $-C(=O)O-R^{17}$, or $-C(=O)NH-R^{17}$, where $R^{22}$ and $R^{23}$ are, independently, $R^{17}$ or together comprise a carbocyclic ring or a heterocyclic ring including the carbon atom to which $R^{22}$ and $R^{23}$ are bonded (preferably $R^{17}$ or $-C(R^{22})(R^{23})COOH$);
   (5) $R^{20}$ is $R^{19}$, halogen, $-Y^1$, or $-CH(Y^2)(R^{17})$ (preferably $R^{19}$ or halogen);
   (6) $Y^1$ is $-C(=O)OR^{21}$, $-C(=O)R^{21}$, $-N(R^{24})R^{21}$, $-S(O)_pR^{29}$, or $-OR^{29}$; and $Y^2$ is $Y^1$ or $-OH$, $-SH$, or $-SO_3H$;
     (a) p is an integer from 0 to 2 (preferably 0);
     (b) $R^{24}$ is hydrogen; alkyl; alkenyl; heteroalkyl; heteroalkenyl; a carbocyclic ring; a heterocyclic ring; $-SO_3H$; $-C(=O)R^{25}$; or, when $R^{18}$ is $-CH(N(R^{24})R^{21})(R^{17})$, $R^{24}$ may comprise a moiety bonded to $R^{21}$ to form a heterocyclic ring; and
     (c) $R^{25}$ is $R^{17}$, $NH(R^{17})$, $N(R^{17})(R^{26})$, $O(R^{26})$, or $S(R^{26})$ (preferably $R^{17}$, $NH(R^{17})$, $N(R^{17})(R^{26})$); where $R^{26}$ is alkyl, alkenyl, a carbocyclic ring, a heterocyclic ring, or (preferably) when $R^{25}$ is $N(R^{17})(R^{26})$, $R^{26}$ may be a moiety bonded to $R^{17}$ to form a heterocyclic ring; and
   (7) $R^{21}$ is $R^{29}$ or hydrogen; where $R^{29}$ is alkyl; alkenyl; arylalkyl; heteroalkyl; heteroalkenyl; heteroarylalkyl; a carbocyclic ring; a heterocyclic ring; or, when Y is $N(R^{24})R^{21}$ and $R^{21}$ is $R^{29}$, $R^{21}$ and $R^{24}$ may together comprise a heterocyclic ring including the nitrogen atom to which $R^{24}$ is bonded (preferably hydrogen, alkyl, a carbocyclic ring, or a heterocyclic ring);

(B) $R^{11}$ is hydrogen, halogen, alkoxy, or $R^{27}C(=O)NH-$ (preferably hydrogen or alkoxy), where $R^{27}$ is hydrogen or alkyl (preferably hydrogen);

(C) bond "a" is a single bond or is nil; and bond "b" is a single bond, a double bond, or is nil; except bond "a" and bond "b" are not both nil;

(D) $R^{12}$ is $-C(R^{8a})-$, or $-CH_2-R^{28}-$ (preferably $-C(R^{8a})-$); where $R^{28}$ is $-C(R^{8a})$, $-O-$, or $-N-$, and $R^{28}$ is directly bonded to N" in Formula (II) to form a 5-membered ring; except, if bond "a" is nil, then $R^{12}$ is (1) (preferably) $-C(R^{8a})(X^1)-$, where
  (i) $X^1$ is $-R^{21}$; $-OR^{30}$; $-S(O)_rR^{30}$, where r is an integer from 0 to 2 (preferably 0); $-OC(=O)R^{30}$; or $N(R^{30})R^{31}$; and
  (ii) $R^{30}$ and $R^{31}$ are, independently, alkyl, alkenyl, carbocyclic ring or heterocyclic ring substituents; or $R^{30}$ and $R^{31}$ together comprise a heterocyclic ring including the nitrogen atom to which $R^{30}$ and $R^{31}$ are bonded; or (2) $-CH_2-R^{32}-$; where $R^{32}$ is $-C(R^{8a})(R^{21})$, $-O-$, or $-NR^{8a}$, and $R^{32}$ is directly bonded to N" in Formula (II) to form a 5-membered ring;

(E) (1) if bond "b" is a single bond, $R^{13}$ is (preferably) $-CH(R^{33})-$; or, $-C(O)NHSO_2-$, if bond "a" is nil; or $-C^*(R^{33})-$ if $R^{14}$ contains a $R^{36}$ moiety; where $R^{33}$ is hydrogen or (preferably) COOH, and C* is linked to $R^{36}$ to form a 3-membered ring;

(2) if bond "b" is a double bond, $R^{13}$ is $-C(R^{33})=$; or (3) if bond "b" is nil, $R^{13}$ is hydrogen, $-SO_3H$, $-PO(OR^{34})OH$, $-C(O)NHSO_2N(R^{34})(R^{35})$, $-OSO_3H$, $-CH(R^{35})COOH$, or $-OCH(R^{34})COOH$ (preferably $-SO_3H$ or $-C(O)NHSO_2N(R^{34})(R^{35})$); where $R^{34}$ is hydrogen, alkyl, alkenyl, a carbocyclic ring, or a heterocyclic ring; and $R^{35}$ is hydrogen, alkyl, alkenyl, or $-NHR^{8a}$; or (preferably), if $R^{13}$ is $-C(O)NHSO_2N(R^{34})(R^{35})$, $R^{34}$ and $R^{35}$ may together comprise a heterocyclic ring including the nitrogen to which $R^{34}$ and $R^{35}$ are bonded; and (F) (1) if bond "a" or bond "b" is nil, then $R^{14}$ is nil;

(2) if bond "a" and "b" are single bonds, $R^{14}$ is $-W-C'''=C(R^{8a})-R^{37}-$, or $-W-C'''(R^{36})-R^{37}-$; or (3) (preferably) if bond "a" is a single bond and bond "b" is a double bond, $R^{14}$ is $-C(R^{8a})(R^{38})-W-C'''-R^{37}-$; or (preferably) $-W'-C(-R^{8a})(R^{38})-C'''-R^{37}-$; or $-W-C'''-R^{37}-$; where (a) W is O; $S(O)_s$, where s is an integer from 0 to 2 (preferably 0); or $C(R^{38})$, where $R^{38}$ is hydrogen, alkyl or alkoxy;
(b) W' is O; or $C(R^{38})$;
(c) $R^{36}$ hydrogen; alkyl; alkenyl; $-COOH$; or, if $R^{13}$ is $-C^*(R^{33})$, $R^{36}$ may be linked to C* to form a 3-membered carbocyclic ring;
(d) $R^{37}$ and is nil, alkyl, alkenyl, a carbocyclic ring, or a heterocyclic ring; and
(e) C''' is directly bonded to $R^{13}$ to form a 5- or 6-membered ring; and (III)(A) L is $-C(=O)-$, and is bonded to $L^3$ and $L^4$
(B) $L^1$ is $L^3$ or $R^{15}L^3$; where
  (1) $L^3$ is nitrogen;

(2) $R^{15}$ is alkyl, alkenyl, heteroalkyl, a heterocyclic ring, a carbocyclic ring, or $R^{15}$ together with $L^3$ is a heteroalkyl or a heterocyclic ring;

(3) $L^3$ is bonded to Q at the point of attachment of $R^1$, $R^6$ or $R^3$, whichever is nil;

(C) $L^2$ is $L^4$, $-X^2_t-R^{39}-L^4$, or $-X^3_t-R^{39}-L^4$; where
(1) $L^4$ is oxygen;
(2) $X^2$ is oxygen, or $S(O)_v$, where v is 0, 1, or 2;
(3) $X^3$ is nitrogen; $N(R^{40})$; $N^+(R^{41})(R^{42})$; or $R^{43}-N(R^{41})$; and is linked to $R^{14}$ by a single or double bond; or, if $R^{14}$ is nil, $X^3$ is linked to B by a single or double bond (preferably $X^3$ is nitrogen, $N(R^{40})$, or $N^+(R^{41})(R^{42})$); where
  (a) $R^{40}$ is $R^{8a}$; $-OR^{8a}$; or $-C(=O)R^{8a}$ (preferably $R^{8a}$);
  (b) $R^{41}$ and $R^{42}$ are, independently, hydrogen; alkyl; alkenyl; carbocyclic rings; heterocyclic rings; or, if $R^6$ is $R^{16}X$, then $R^{41}$ and $R^{42}$ together with Q" may comprise a heterocyclic ring as $R^{16}$;
  (c) $R^{43}$ is $N(R^{41})$, oxygen or sulfur;
(4) t is 0 or 1;
(5) $R^{39}$ is alkyl, alkenyl, heteroalkyl, heteroalkenyl, a carbocyclic ring, or a heterocyclic ring;
(6) (a) if bond "a" or bond "b" is nil, then $L^2$ is bonded directly to $R^{12}$ or $R^{13}$; or
  (b) if bond "a" and bond "b" are not nil, then $L^2$ is bonded to $R^{14}$;

and pharmaceutically-acceptable salts and biohydrolyzable esters thereof, and hydrates thereof. Preferred antimicrobial compounds made by the processes of this invention include those where $R^3$ is nil and comprises a bond to $L^1$, and those where $R^6$ is nil and comprises a bond to $L^1$.

Definitions and Usage of Terms

The following is a list of definitions for terms used herein.

"Heteroatom" is a nitrogen, sulfur or oxygen atom. Groups containing one or more heteroatoms may contain different heteroatoms.

"Alkyl" is an unsubstituted or substituted saturated hydrocarbon chain radical having from 1 to 8 carbon atoms, preferably from 1 to 4 carbon atoms. Preferred alkyl groups include (for example) methyl, ethyl, propyl, isopropyl, and butyl.

"Heteroalkyl" is an unsubstituted or substituted saturated chain radical having from 3 to 8 members comprising carbon atoms and one or two heteroatoms.

"Alkenyl" is an unsubstituted or substituted hydrocarbon chain radical having from 2 to 8 carbon atoms, preferably from 2 to 4 carbon atoms, and having at least one olefinic double bond.

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Cycloalkyl" is a saturated carbocyclic ring radical. Preferred cycloalkyl groups include (for example) cyclopropyl, cyclobutyl and cyclohexyl.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems.

Monocyclic rings contain from 3 to 9 atoms, preferably 3 to 6 atoms. Polycyclic rings contain from 7 to 17 atoms, preferably from 7 to 13 atoms.

"Aryl" is an aromatic carbocyclic ring radical. Preferred aryl groups include (for example) phenyl, tolyl, xylyl, cumenyl and naphthyl.

"Heteroaryl" is an aromatic heterocyclic ring radical. Preferred heteroaryl groups include (for example) thienyl, furyl, pyrrolyl, pyridinyl, pyrazinyl, thiazolyl, quinolinyl, pyrimidinyl and tetrazolyl.

"Alkoxy" is an oxygen radical having a hydrocarbon chain substituent, where the hydrocarbon chain is an alkyl or alkenyl (i.e., —O—alkyl or —O—alkenyl). Preferred alkoxy groups include (for example) methoxy, ethoxy, propoxy and allyloxy.

"Alkylamino" is an amino radical having one or two alkyl substituents (i.e., —N—alkyl).

"Arylalkyl" is an alkyl radical substituted with an aryl group. Preferred arylalkyl groups include benzyl and phenylethyl.

"Arylamino" is an amine radical substituted with an aryl group (i.e., —NH—aryl).

"Aryloxy" is an oxygen radical having a aryl substituent (i.e., —O—aryl).

"Acyl" or "carbonyl" is a radical formed by removal of the hydroxy from an carboxylic acid (i.e., R—C(=O)—). Preferred alkylacyl groups include (for example) acetyl, formyl, and propionyl.

"Acyloxy" is an oxygen radical having an acyl substituent (i.e., —O—acyl); for example, —O—C(=O)—alkyl.

"Acylamino" is an amino radical having an acyl substituent (i.e., —N—acyl); for example, —NH—C(=O)—alkyl.

"Halo", "halogen", or "halide" is a chloro, bromo, fluoro or iodo atom radical. Chloro and fluoro are preferred halides.

Also, as referred to herein, a "lower" hydrocarbon moiety (e.g., "lower" alkyl) is a hydrocarbon chain comprised of from 1 to 6, preferably from 1 to 4, carbon atoms.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium). Preferred anionic salts include the halides (such as chloride salts).

A "biohydrolyzable ester" is an ester of a QLA that does not essentially interfere with the antimicrobial activity of the compounds, or that are readily metabolized by a human or lower animal subject to yield an antimicrobially-active quinolonyl lactam. Such esters include those that do not interfere with the biological activity of quinolone antimicrobials or beta-lactam antimicrobials (cephems, for example). Many such esters are known in the art, as described in World Patent Publication 87/05297, Johnston et al., published Sep. 11, 1987, (incorporated by reference herein). Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkyl acylamino alkyl esters (such as acetamidomethyl esters).

As defined above and as used herein, substituent groups may themselves be substituted. Such substitution may be with one or more substituents. Such substituents include (for example) those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

Also, as used in defining the structure of the compounds of this invention, a particular radical may be defined for use as a substituent in multiple locations. For example, the $R^8$ substituent is defined as a potential substituent of $R^7$, but is also incorporated into the definition of other substituents (such as $R^1$, $R^6$, and $R^{10}$. As used herein, such a radical is independently selected each time it is used (e.g., $R^8$ need not be alkyl in all occurrences in defining a given compound of this invention).

Lactam-containing moiety

Groups $R^{12}$, $R^{13}$, and $R^{14}$, together with bonds "a" and "b" of formula (I), form any of a variety of lactam-containing moieties known in the art to have antimicrobial activity. Such moieties wherein either bond "a" or bond "b" are nil (i.e., do not exist) are monocyclic; if both bonds exist, the structures are bi-cyclic. Preferably, bond "a" is a single bond and bond "b" is a double bond.

Preferred lactam moieties include the oxacephems and carbacephems of the representative formula:

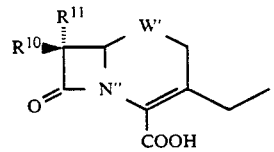

wherein, referring to formula (II), bond "a" is a single bond; bond "b" is a double bond; $R^{12}$ is —C($R^{8a}$)—, where $R^{8a}$ is hydrogen; $R^{13}$ is —CH($R^{33}$), where $R^{33}$ is COOH; and $R^{14}$ is —W'—C($R^{8a}$)($R^{38}$)—C'''—$R^{37}$, where $R^{8a}$ and $R^{38}$ are hydrogen, $R^{37}$ is methylene, and W' is O (for oxacephems) or C($R^{38}$) (for carbacephems).

Other preferred lactam moieties include the isocephems and iso-oxacephems of the representative formula:

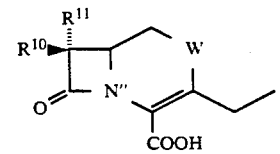

wherein, referring to formula II, bond "a" is a single bond; bond "b" is a double bond; $R^{12}$ is —C($R^{8a}$) where $R^{8a}$ is hydrogen; $R^{13}$ is —C($R^{33}$)=, where $R^{33}$ is COOH; and $R^{14}$ is —C($R^{8a}$)($R^{38}$)—W—C'''—$R^{37}$ where $R^{8a}$ and $R^{38}$ are each hydrogen, $R^{37}$ is methylene, and W is S (for isocephems) or O (for iso-oxacephems).

Other preferred lactam-containing moieties include the penems, carbapenems and clavems, of the representative formula:

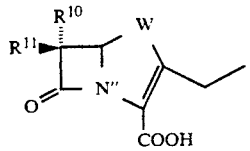

wherein, referring to formula (II), bond "a" is a single bond; bond "b" is a double bond; $R^{12}$ is —$C(R^{8a})$, where $R^{8a}$ is hydrogen; $R^{13}$ is —$C(R^{33})$=, where $R^{33}$ is COOH; and $R^{14}$ is —W—C'''—$R^{37}$, where $R^{37}$ is methylene, and W is S (for penems), $C(R^{38})$ (for carbapenems), or O (for clavems). Such lactam moieties are described in the following articles, all incorporated by reference herein: R. Wise, "n Vitro and Pharmacokinetic Properties of the Carbapenems", 30 *Antimicrobial Agents and* Chemotherapy 343 (1986); and S. McCombie et al., "Synthesis and In Vitro Activity of the Penem Antibiotics", 8 *Medicinal Research Reviews* 393 (1988).

Other preferred lactam-containing moieties of this invention include the penicillins of the representative formula:

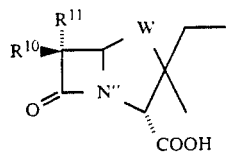

wherein, referring to formula II, bond "a" is a single bond, bond "b" is a single bond; $R^{12}$ is —$C(R^{8a})$—, where $R^{8a}$ is hydrogen; $R^{13}$ is —$CH(R^{33})$— where $R^{33}$ is COOH; and $R^{14}$ is —W—C'''($R^{36}$)—$R^{37}$— where $R^{36}$ is methyl, $R^{37}$ is methylene, and W is S.

Other preferred lactam-containing moieties include the monocyclic beta-lactams, of the representative formula:

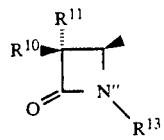

wherein, referring to formula (II), bond "a" is a single bond; bond "b" is nil; $R^{12}$ is —$C(R^{8a})$—, where $R^{8a}$ is hydrogen; $R^{14}$ is nil; and $R^{13}$ is —$SO_3H$ (for a monobactam), —$PO(OR^{34})OH$ (for a monophospham); —C(O)$NHSO_2N(R^{34})(R^{35})$ (for a monocarbam), —$OSO_3H$ (for a monosulfactam), —$CH(R^{35})COOH$ (for nocardicins), or —$OCH(R^{34})COOH$. Such lactam moieties are described in C. Cimarusti et al., "Monocyclic 8-lactam Antibiotics", 4 *Medicinal Research Reviews* 1 (1984), incorporated by reference herein.

Other preferred lactam moieties include the monocyclic beta-lactams of the representative formula:

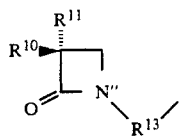

wherein referring to formula II, bond "a" is nil, bond "b" is a single bond; $R^{12}$ is —$C(R^{8a})(R^{29})$— where both $R^{8a}$ and $R^{29}$ are hydrogen; and $R^{14}$ is nil.

Other preferred lactam moieties include the clavams of the representative formula:

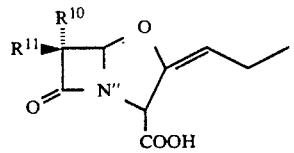

wherein, referring to formula (II), bond "a" is a single bond; bond "b" is a single bond; $R^{12}$ is —$C(R^{8a})$—, where $R^{8a}$ is hydrogen; $R^{13}$ is —$CH(R^{33})$—, where $R^{33}$ is COOH; and $R^{14}$ is W—C'''=C—($R^{8a}$)—$R^{37}$, where $R^{8a}$ is hydrogen and $R^{37}$ is methylene, and W is O.

Other preferred lactam moieties include the 2,3-methylenopenams and -carbapenams of the representative formula:

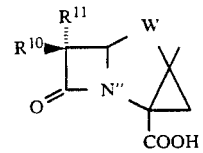

wherein, referring to formula (II), bond "a" is a single bond; bond "b" is a single bond; $R^{12}$ is —$C(R^{8a})$—, where $R^{8a}$ is hydrogen; $R^{13}$ is —$C^*(R^{33})$, where $R^{33}$ is COOH; and $R^{14}$ is W—C'''($R^{36}$)—$R^{37}$, where $R^{37}$ is nil, $R^{36}$ is linked to C* to form a 3-membered carbocyclic ring, and W is $C(R^{38})$ or sulfur.

Lactam moieties of this invention also include the lactivicin analogs of the representative formula:

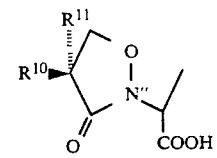

wherein, referring to formula (II), bond "a" is nil bond "b" is a single bond; $R^{12}$ is —$CH_2$—$R^{32}$, where $R^{32}$ is O; $R^{13}$ is —$CH(R^{33})$—, where $R^{33}$ is COOH; and $R^{14}$ is nil.

Other lactam moieties include the pyrazolidinones of the representative formula:

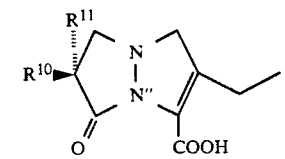

wherein, referring to formula (I), bond "a" is a single bond; bond "b" is a double bond; $R^{12}$ is —$CH_2$—$R^{28}$—, where $R^{28}$ is —N—; $R^{13}$ is —$C(R^{33})$—, where $R^{33}$ is COOH; and $R^{14}$ is W—C'''—$R^{37}$—, where $R^{37}$ is methylene, and W is $C(R^{38})$.

Other lactam moieties include the gama-lactams of the representative formula:

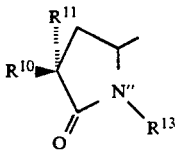

wherein, referring to formula (II), bond "a" is a single bond; bond "b" is nil; $R^{12}$ is —$CH_2$—$R^{28}$—, where $R^{28}$ is —$C(R^{8a})$ and $R^{8a}$ is hydrogen; $R^{13}$ is —$SO_3H$, —PO-$(OR^{34})OH$, —$C(O)NHSO_2N(R^{34})(R^{35})$, —$OSO_3H$, —$CH(R^{35})COOH$, or —$OCH(R^{34})COOH$; and $R^{14}$ is nil.

Preferred lactam-containing moieties include isocephems, iso-oxacephems, oxacephems, carbacephems, penicillins, penems, carbapenems, and monocyclic beta-lactams. More preferred are penems, carbapenems and monocyclic beta-lactams. Particularly preferred lactam-containing moieties for compounds made by this invention are penems.

$R^{10}$, in formula (II), is any radical that may be substituted at the active stereoisomeric position of the carbon adjacent to the lactam carbonyl of an antimicrobially-active lactam. (As used herein, the term "antimicrobially-active lactam" refers to a lactam-containing compound, without a quinolonyl substituent moiety, which has antimicrobial activity.) This "active" position is beta (i.e., 7-beta) for oxacephems and carbacephems (for example). The active position is alpha for penems, carbapenems, clavems and clavams.

Appropriate $R^{10}$ groups will be apparent to one of ordinary skill in the art. Many such $R^{10}$ groups are known in the art, as described in the following documents (all of which are incorporated by reference herein): *Cephalosporins and Penicillins: Chemistry and Biology* (E. Flynn, editor, 1972); *Chemistry and Biology of b-Lactam Antibiotics* (R. Morin et al., editors, 1987); "The Cephalosporin Antibiotics: Seminar-in-Print", 34 *Drugs* (Supp. 2) 1 (J. Williams, editor, 1987); *New Beta-Lactam Antibiotics: A Review from Chemistry of Clinical Efficacy of the New Cephalosporins* (H. Neu, editor, 1982); M. Sassiver et al., in *Structure Activity Relationships among the Semi-synthetic Antibiotics* (D. Perlman, editor, 1977). W. Durckheimer et al., "Recent Developments in the Field of Beta-Lactam Antibiotics", 24 *Angew. Chem. Int. Ed. Engl.* 180 (1985); G. Rolinson, "Beta-Lactam Antibiotics", 17 *J. Antimicrobial Chemotherapy* 5 (1986); European Patent Publication 187,456, Jung, published Jul. 16, 1986; and World Patent Publication 87/05297, Johnston et al., published Sep. 11, 1987.

For penems, carbapenems, clavems and clavams, $R^{10}$ is preferably lower alkyl, or hydroxy-substituted lower alkyl. Particularly preferred $R^{10}$ groups include hydrogen, hydroxymethyl, ethyl, [1(R)-hydroxyethyl], [I(R)-[(hydroxysulfonyl)oxyethyl]], and [1-methyl-l-hydroxyethyl].

Except for penems, carbapenems, clavems and clavams, preferred $R^{10}$ groups are amides, such as: acetylamino, preferably substituted with aryl, heteroaryl, aryloxy, heteroarylthio and lower alkylthio substituents; arylglycylamino, preferably N-substituted with heteroarylcarbonyl and cycloheteroalkylcarbonyl substituents; arylcarbonylamino; heteroarylcarbonylamino; and lower alkoxyiminoacetylamino, preferably substituted with aryl and heteroaryl substituents. Particularly preferred $R^{10}$ groups include amides of the general formula $R^{18}$—$(CH_2)_m$—$C(=O)NH$— and $R^{18}$ is $R^{17}$. Examples of such preferred $R^{10}$ groups include:
[(2-amino-5-halo-4-thiazolyl)acetyl]amino;
[(4-aminopyridin-2-yl)acetyl]amino;
[[(3,5-dichloro-4-oxo-1(4H)-pyridinyl)acetyl]amino];
[[[2-(aminomethyl)phenyl]acetyl]amino];
[(1H-tetrazol-1-ylacetyl)amino];
[(cyanoacetyl)amino];
[(2-thienylacetyl)amino];
[[(2-amino-4-thiazoyl)acetyl]amino]; and
sydnone, 3-[-2-amino]-2-oxoethyl.

When $R^{10}$ is $R^{18}$—$(CH_2)_m$—$C(C=O)NH$—, and $R^{18}$ is —$Y^1$, preferred $R^{10}$ groups include the following:
[sulfamoylphenylacetyl]amino;
[[(4-pyridinylthio)acetyl]amino];
[[[(cyanomethyl)thio]acetyl]amino];
(S)-[[[(2-amino-2-carboxyethyl)thio]acetyl]amino];
[[[(trifluoromethyl)thio]acetyl]amino]; and
(E)-[[[(2-aminocarbonyl-2-fluoroethenyl)thio]acetyl]amino).

When $R^{10}$ is $R^{18}$—$(CH_2)_m$—$C(=O)NH$—, and $R^{18}$ is —$CH(Y^2)(R^{17})$, preferred $R^{10}$ groups include the following:
[carboxyphenylacetyl]amino;
[(phenoxycarbonyl)phenylacetyl]amino;
[4-methyl-2,3-dioxo-l-piperazinecarbonyl-D-phenylglycyl]amino;
[[[3-(2-furylmethyleneamino)-2-oxo-l-imidazolidinyl]-carbonyl]amino]phenyl]acetyl]amino;
(R)-[(aminophenylacetyl)amino];
(R)-[[amino(4-hydroxyphenyl)acetyl]amino];
(R)-[(amino-1,4-cyclohexadien-l-yl)acetyl)amino];
[(hydroxyphenylacetyl)amino];
(R)-[[[[(4-ethyl-2,3-dioxo-l-piperazinyl)carbonyl]amino](4-hydroxyphenyl)acetyl]amino];
(R)-[[[[(5-carboxy-1H-imidazol-4-yl)carbonyl]amino]-phenylacetyl]amino];
(R)-[[[[(4-hydroxy-6-methyl-3-pyridinyl)carbonyl]amino](4-hydroxyphenyl)acetyl]amino];
(R)-[(phenylsulfoacetyl)amino];
(2R,3S)-[[2-[[(4-ethyl-2,3-dioxo-l-piperazinyl)carbonyl]amino]-3-hydroxy-1-oxobutyl]amino];
[[carboxy(4-hydroxyphenyl)acetyl]amino];
(R)-[[amino[3-[(ethylsulfonyl)amino]phenyl]acetyl]amino];
(R)-[[amino(benzo[b]thien-3-yl)acetyl]amino];
(R)-[[amino(2-naphthyl)acetyl]amino);
(R)-[[amino(2-amino-4-thiazolyl)acetyl]amino];
[([[(6,7-dihydroxy-4-oxo-4H-l-benzopyran-3-yl)carbonyl]amino](4-hydroxyphenyl)acetyl]amino];
(R,R)-[[2-[4-[2-amino-2-carboxyethyloxycarbonyl]aminophenyl]-2-hydroxyacetyl]amino]; and
(S)-[[(5-hydroxy-4-oxo-1(4H)-pyridin-2-yl)carbonylamino(2-amino-4-thiazolyl)acetyl]amino].

Another preferred $R^{10}$ group is $R^{17}$—$C(=CHR^2$-0)—$C(=O)NH$—. Another class of preferred $R^{10}$ groups (for lactam-containing moieties other than penems, carbapenems, clavems and clavams) include those of the formula:

$R^{17}$—C(=NO—$R^{19}$)—C(=O)NH—.

Examples of this preferred class of $R^{10}$ groups include:
2-phenyl-2-hydroxyiminoacetyl;
2-thienyl-2-methoxyiminoacetyl; and
2-[4-(gamma-D-glutamyloxy)phenyl]-2-hydroxyiminoacetyl.
(Z)[[(2-amino-4-thiazolyl)(methoxyimino)acetyl]amino];
[[(2-furanyl(methoxyimino)acetyl]amino];
(Z)-[[(2-amino-4-thiazolyl)[(l-carboxy-l-methyl)ethoxyimino]acetyl]amino];
(Z)-[[(2-amino-4-thiazolyl)(1-carboxymethoxyimino)acetyl]amino];
[[(2-amino-4-thiazolyl)[(IH-imidazol-4-ylmethoxy)imino]acetyl]amino];
(Z)-[[(2-amino-4-thiazolyl-3-oxide)(methoxyimino)acetyl]amino]; and
(S,Z)-[[(2-amino-4-thiazolyl)[carboxy(3,4-dihydroxyphenyl)methoxyimino]acetyl]amino].

Suitable $R^{11}$ groups are among those well-known in the art, including those defined in the following documents (all incorporated by reference herein). W. Durckheimer et al., "Recent Developments in the Field of Beta-Lactam Antibiotics", 24 *Angew. Chem. Int. Ed. Engl.* 180 (1985); G. Rolinson, "Beta-Lactam Antibiotics", 17 *J. Antimicrobial Chemotherapy* 5 (1986); and European Patent Publication 187,456, Jung, published Jul. 16, 1986. Preferred $R^{11}$ groups include hydrogen, methoxy, ethoxy, propoxy, thiomethyl, halogen, cyano, formyl and formylamino. Particularly preferred $R^{11}$ groups include hydrogen, methoxy, halogen, and formylamino.

Quinolone Moieties

Groups $A^1$, $A^2$, $A^3$, $R^1$, $R^3$, and $R^4$ of formula I form a moiety (herein, "quinolone moiety") present in any of a variety of quinolone, naphthyridine or related heterocyclic compounds known in the art to have antimicrobial activity. Such heterocyclic moieties are well known in the art, as described in the following articles, all incorporated by reference herein: J. Wolfson et al., "The Fluoroquinolones: Structures, Mechanisms of Action and Resistance, and Spectra of Activity In Vitro", 28 *Antimicrobial Agents and Chemotherapy* 581 (1985); and T. Rosen et al., 31 *J. Med Chem.* 1586 (1988) ; T. Rosen et al ., 31 *J. Med. Chem.* 1598 (1988); G. Klopman et al., 31 *Antimicrobe Agents Chemother.* 1831 (1987); 31:1831–1840; J. P. Sanchez et al., 31 *J. Med. Chem.* 983 (1988); J. M. Domagala et al., 31 *J. Med. Chem.* 991 (1988); M. P. Wentland et al., in 20 *Ann. Rep. Med. Chem.* 145 (D. M. Baily, editor, 1986); J. B. Cornett et al., in 21 *Ann. Rep. Med. Chem.* 139 (D. M. Bailey, editor, 1986); P. B. Fernandes et al., in 22 *Ann. Rep. Med. Chem.* 117 (D. M. Bailey, editor, 1987); R. Albrecht, 21 *Prog. Drug Research* 9 (1977); and P. B. Fernandes et al., in 23 *Ann. Rep. Med. Chem. (R. C. Allen, editor,* 1987).

Preferred quinolone moieties include those where $A^1$ is $C(R^7)$, $A^2$ is $C(R^2)$, and $A^3$ is $C(R^5)$ (i.e., quinolones); $A^1$ is nitrogen, $A^2$ is $C(R^2)$, and $A^3$ is $C(R^5)$ (i.e., naphthyridines); $A^1$ is $C(R^7)$, $A^2$ is $C(R^2)$, and $A^3$ is nitrogen (i.e., cinnoline acid derivatives); and where $A^1$ is nitrogen, $A^2$ is nitrogen, and $A^3$ is $C(R^5)$ (i.e., pyridopyrimidine derivatives). More preferred quinolone moieties are those where $A^1$ is $C(R^7)$, $A^2$ is $C(R^2)$, and $A^3$ is $C(R^5)$ (i.e., quinolones); and where $A^1$ is nitrogen, $A^2$ is $C(R^2)$, and $A^3$ is $C(R^5)$ (i.e., naphthyridines). Particularly preferred quinolone moieties are where $A^1$ is $C(R^7)$, $A^2$ is $C(R^2)$, and $A^3$ is $C(R^5)$ (i.e., quinolones).

$R^1$ is preferably alkyl, aryl, cycloalkyl and alkylamino. More preferably, $R^1$ is ethyl, 2-fluoroethyl, 2-hydroxyethyl, t-butyl , 4-fluorophenyl, 2,4-difluorophenyl, methylamino and cyclopropyl. Cyclopropyl is a particularly preferred $R^1$ group. Preferred quinolone moieties also include those where $A^1$ is $C(R^7)$ and $R^1$ and $R^7$ together comprise a 6-membered heterocyclic ring containing an oxygen or sulfur atom.

$R^2$ is preferably hydrogen or halo. More preferably $R^2$ is chlorine or fluorine. Fluorine is a particularly preferred $R^2$ group.

Preferred $R^3$ groups include nitrogen-containing heterocyclic rings. Particularly preferred are nitrogen-containing heterocyclic rings having from 5 to 8 members. The heterocyclic ring may contain additional heteroatoms, such as oxygen, sulfur, or nitrogen, preferably nitrogen. Such heterocyclic groups are described in U.S. Pat. No. 4,599,334, Petersen et al., issued Jul. 8, 1986; and U.S. Pat. No. 4,670,444, Grohe et al., issued Jun. 2, 1987 (both incorporated by reference herein). Preferred $R^3$ groups include unsubstituted or substituted pyridine, piperidine, morpholine, diazabicyclo[3.1.1]heptane, diazabicyclo[2.2.1]heptane, diazabicyclo[3.2.1]octane, diazabicyclo[2.2.2]octane, thiazolidine, imidazolidine, pyrrole and thiamorpholine, as well as the following particularly preferred $R^3$ groups include piperazine, 3-methylpiperazine, 3-aminopyrrolidine, 3-aminomethylpyrrolidine, N,N-dimethylaminomethylpyrrolidine, N-methylaminomethylpyrrolidine, N-ethylaminomethylpyrrolidine, pyridine, N-methylpiperazine, and 3,5-dimethylpiperazine.

The specific physical, chemical, and pharmacological properties of the quinolonyl lactams of this invention may depend upon the particular combination of the integral lactam-containing moiety, quinolone moiety and linking moiety comprising the compound. For example, selection of particular integral moieties may affect the relative susceptibility of the quinolonyl lactam to bacterial resistance mechanisms (e.g., beta-lactamase activity).

Preferred lactam moieties, quinolone moieties, and QLAs are described in the following documents, all of which are incorporated by reference herein: European Patent Publication 366,189, White and Demuth, published May 2, 1990; European Patent Publication 335, 297, Albrecht et al., published October 4, 1989.

Methods of Manufacture

The processes of this invention comprise the steps of:

(1) Reacting a lactam compound of the formula B-$L^4$-H with phosgene to form an intermediate compound of the formula B—$L^4$—C(=O)—Cl; and (2) Coupling said intermediate compound with a quinolone compound of the formula Q-$L^3$-$R^{44}$; wherein $R^{44}$ is hydrogen, $Si(R^{45})_3$, or $Sn(R^{45})_3$; and $R^{45}$ is lower alkyl.

Preferably, these processes additionally comprise steps for protecting the lactam and quinolone compounds prior to the reacting and coupling steps. In particular, the carboxylate groups at $R^4$ and $R^{13}$ are protected, using an ester group. The compound formed following the coupling step is then deprotected, by removal of the ester groups, to yield the free acid compound.

Accordingly, a preferred process of this invention additionally comprises:

(a) a step, prior to said reacting step, wherein an ester of said lactam compound is formed;
(b) a step, prior to said coupling step, wherein an ester of said quinolone compound is formed; and
(b) deprotection steps, after said coupling step, wherein said groups are removed.

Suitable hydrolyzable esters useful in such protection steps are well known in the art. They include, for example, allyl, benzyl, p-methoxybenzyl, p-nitrobenzyl, diphenylmethyl, methyl, ethyl, 2,2,2-trichloroethyl, 2-trimethylsilylethyl, 2-methylthioethyl, trimethylsilyl, t-butyldiphenylsilyl, t-butyl, and tributylstannyl esters. Such esters, and suitable protection and deprotection chemistry for carboxylates and other functional groups, are described in T. W. Greene, *Protective Groups in Organic Synthesis*, J. Wiley and Sons (1981), incorporated by reference herein.

Further, depending on the specific lactam compounds and quinolone compounds employed, other functional groups (e.g., the $R^{10}$ substituent or the lactam compound) may need to be protected or blocked in order to prevent undesired competing side reactions from occurring during the coupling step. Protecting groups for hydroxyl substituents include ethers, esters, and carbonates; and protecting groups for amino substituents include carbamates, and amides. If various protecting groups are employed, then an appropriate deprotecting step, that will not decompose the coupled conjugate, may be required to obtain antibacterially active products. Chemistry useful in the protecting and deprotecting steps are well known in the chemical literature.

In a preferred process, a silylated quinolone compound is used in the coupling step, wherein $R^{44}$ of the quinolone compound is $Si(R^{45})_3$, and $R^{45}$ is lower alkyl. Preferably $R^{45}$ is methyl or ethyl. Also, the $R^{45}$ groups may be independently selected, such that the $Si(R^{45})_3$ moiety need not contain three identical $R^{45}$ substituents.

Any of a number of silylating reagents known in the art may be used to form the silylated quinolone compound, by reacting the silylating agent with a quinolone compound wherein $R^{44}$ is hydrogen. Such silylating reagents include, for example, chlorotrimethylsilane; N-methyl-N-trimethylsilyl-trifluoroacetamide; N,N-bis(trimethylsilyl)urea; 1-trimethylsilylimidazole; bis(trimethylsilyl)trifluoroacetamide; and N,O-bis(trimethylsilyl)acetamide. Further, use of the silylating agent to form a silylated quinolone compound may also yield a silyl ester of $R^4$ carboxylate of the quinolone, as a protecting group. This ester can then be removed, using well-known deprotection chemistry.

The reacting step and coupling step are carried out in solution, using any of a variety of suitable solvents. Such solvents include, for example: halocarbon solvents, such as methylene chloride, chloroform, and dichloroethane; ethers, such as diethyl ether and tetrahydrofuran (THF); aromatic solvents, such as benzene and toluene; and mixtures thereof. Halocarbon solvents are preferred. Preferably the coupling step comprises adding a solution containing the quinolone compound to a solution containing the intermediate compound.

The reacting step and coupling step are preferably conducted at low temperatures, from −92° C. to about 22° C. Preferably the temperatures are from about −80° C. to about 0° C., more preferably from about −80° C. to about −40° C. Preferably, reagents are mixed in the reaction step and coupling step so as to allow control of the temperature within these ranges.

Procedures for making a broad variety of lactam and quinolone starting materials are well known in the art. For example, procedures for preparing lactam-containing moieties are described in the following references, all incorporated by reference herein (including articles cited within these references): *Cephalosporins and Penicillins: Chemistry and Biology* (E. H. Flynn, ed, 1972) Chapters 2, 3, 4, 5, 6, 7, 15 and Appendix I; *Recent Advances in the Chemistry of β-Lactam Antibiotics* (A.G. Brown and S. M. Roberts, ed., 1985); *Topics in Antibiotic Chemistry*, Vol . 3, (Part B) and Vol . 4, (P. Sommes, ed., 1980); *Recent Advances in the Chemistry of β-lactam Antibiotics* (J. Elks, ed., 1976); *Structure-Activity Relationships Among the Semisynthetic Antibiotics* (D. Perlman, ed, 1977); Chapts. 1, 2, 3, 4; *Antibiotics, Chemotherapeutics and Antibacterial Agents for Disease Control* (M. Grayson, ed, 1982); Chemistry and Biology of β-Lactam Antibiotics, Vols 1-3 (K. B. Morin and M. Gorman, eds, 1982); 4 *Medicinal Research Reviews* 1-24 (1984); 8 *Medicinal Research Review* 393-440 (1988); 24 *Angew. Chem. Int. Ed. Engl.* 180-202 (1985); 40 *J. Antibiotics* 182-189 (1987); European Patent Publication 266,060; 42 *J. Antibiotics* 993 (1989); U.S. Pat. No. 4,742,053; 35 *Chem. Pharm. Bull.* 1903-1909 (1987); 32 *J. Med. Chem.*, 601-604 (1989); U.S. Pat. No. 4,791,106; Japanese Patent Publication 62/158291; 31 *J. Med. Chem.* 1987-1993 (1988); 30 *J. Med. Chem.*, 514-522 (1987); 28 *Tet. Let.* 285-288 (1987); 28 *Tet. Let.* 289-292 (1987); 52 *J. Org. Chem.*, 4007-4013 (1987); 40 *J. Antibiotics*, 370-384 (1987); 40 *J. Antibiotics*, 1636-1639 (1987); 37 *J. Antibiotics*, 685-688 (1984); 23 *Heterocycles*, 2255-2270; 27 *Heterocycles*, 49-55; 33 *Chem. Pharm. Bull.* 4371-4381 (1985); 28 *Tet. Let*, 5103-5106 (1987); 53 *J. Org. Chem.*, 4154-4156 (1988); 39 *J. Antibiotics*, 1351-1355 (1986); 59 *Pure and Appl. Chem.*, 467-474 (1987); 1987 *J.C.S. Chem. Comm.*; 44 Tetrahedron, 3231-3240 (1988); 28 *Tet. Let.*, 2883-2886, (1987); 40 *J. Antibiotics*, 1563-1571 (1987); 33 *Chem. Pharm. Bull.*, 4382-4394 (1985); 37 *J. Antibiotics*, 57-62 (1984); U.S. Pat. No. 4,631,150; 34 *Chem. Pharm. Bull.*, 999-1014 (1986); 52 *J. Org. Chem.*, 4401-4403 (1987); 39 *Tetrahedron*, 2505-2513 (1983); 38 *J. Antibiotics*, 1382-1400 (1985); European Patent Application 053,815; 40 *J. Antibiotics*, 1563-1571 (1987); 40 *J. Antibiotics*, 1716-1732 (2987); 47 *J. Org. Chem.*, 5160-5167 (1981); U.S. Pat. No. 4,777,252; U.S. Pat. No. 4,762,922; European Patent Publication 287,734; U.S. Pat. No. 4,762,827; European Patent Publication 282,895; European Patent Publication 282,365; and U.S. Pat. No. 4,777,673.

General procedures for preparing quinolone compounds useful in the methods of this invention are described in the following references, all incorporated by reference herein (including articles listed within these references); 21 *Progress in Drug Research*, 9-104 (1977); 31 *J. Med. Chem.*, 503-506 (1988); 32 *J. Med. Chem.*, 1313-1318 (1989); 1987 *Liebigis Ann. Chem.*, 871-879 (1987); 14 *Drugs Exptl. Clin. Res.*, 379-383 (1988); 31 *J. Med. Chem.*, 983-991 (1988); 32 *J. Med. Chem.*, 537-542 (1989); 78 *J. Pharm. Sci.*, 585-588 (1989); 26 *J. Het. Chem.*, (1989); 24 *J. Het. Chem.*, 181-185 (1987); U.S. Pat. No. 4,599,334, 35 *Chem. Phatm. Bull.*, 2281-2285 (1987); 29 *J. Med. Chem.*, 2363-2369 (1986); 31 *J. Med. Chem.*, 991-1001 (1988); 25 *J. Het. Chem.*, 479-485 (1988); European Patent Publication 266,576; European Patent Publication 251,308, 36 *Chem. Pharm. Bull.*, 1223-1228 (1988); European Patent Publication 227,088; European Patent Publication 227,039; European Patent Publication 228,661; 31 *J. Med. Chem.*, 1586-1590 (1988); 31 *J. Med. Chem.*, 1598-1611 (1988); and 23 *J. Med. Chem.*, 1358-1363 (1980). Preparation of quinolone compounds useful herein are also described in: European Patent Publication 366,189, White and Demuth, published May 2, 1990; European Patent Publication 335,297, Albrecht et al., published Oct. 4, 1989; incorporated by reference herein.

The following non-limiting examples illustrate the processes of the present invention.

EXAMPLE 1

Preparation of [5R-[5a,6a]]-3-[[[4-(3-Carboxyl-1-cyclopropyl-6-fluoro-1,4-dihydro-4-oxo-7-quinolinyl)-1-piperazinyl]carbonyloxy]methyl]-6-[(R)-1-hydroxyethyl]-7-oxo-4-thia-1-azabicyclo[3.2.0]hept-2-ene-2-carboxylic Acid Disodium Salt funnel. The apparatus is dried and then cooled to approximately $-78°$ C. under nitrogen with a dry ice/acetone bath. Phosgene (60 mL, 20% in toluene) is added via syringe through the dropping funnel. Dichloromethane is then rinsed through the dropping funnel into the flask. A solution of [5R-[5a,6a]]-6-[(R)-1-(t-butyl-dimethylsilyl-oxy)ethyl]-3-hydroxymethyl-7-oxo-4-thia-1-azabicyclo[3.2.0]hept-2-ene-2-carboxylic acid allyl ester (40 gram) and N,N-diisopropylethylamine (20 ml) in 150 mL dichloromethane is transferred via cannula to the dropping funnel on the 1 L flask. This solution is then added to the phosgene solution at such a rate as to maintain the solution temperature between $-75°$ C. and $-70°$ C. (approximately 2.5 hour). Separately, N-methyl-N-trimethylsilyl-trifluoroacetamide (56 ml) is added to a suspension of 1-cyclopropyl-6-fluoro-1,4-dihydro-4-oxo-7-(1-piperazinyl)-3-quinoline carboxylic acid (33.2 gram) in 250 mL dichloromethane

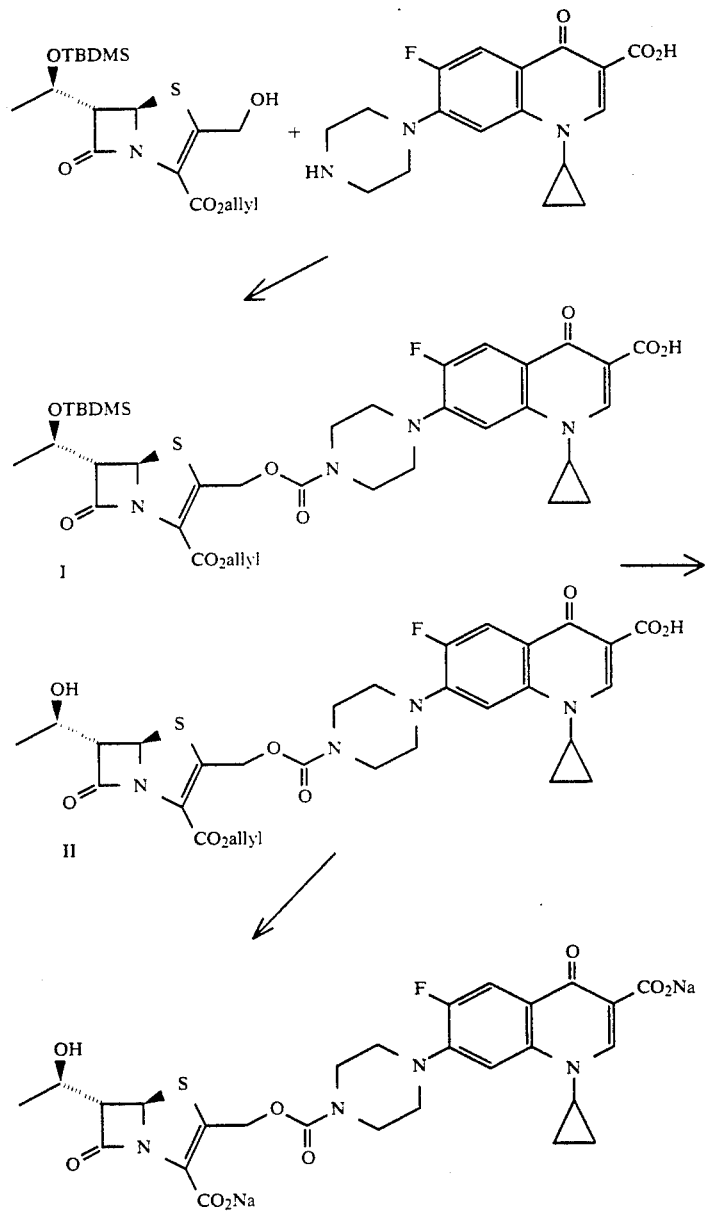

A 3-neck, 1 L flask is fitted with a low temperature thermometer, overhead stirrer and a 500 mL dropping at room temperature. The resulting solution is transferred to the dropping funnel on the 1 L flask via cannula and is added to the reaction mixture at such a rate so as to maintain the reaction temperature between −75° C. and −70° C. over approximately 1.5 hour. The reaction mixture is stirred for approximately 15 minutes, the cooling bath is removed and 50 mL of water is added, allowing the solution to warm to approximately −10° C. A second aliquot of water (50 mL) is added and the mixture is further warmed to 10° C.

The solution is filtered, extracted with water, washed with brine, dried over sodium sulfate and concentrated to approximately 200 mL volume in vacuo. With overhead stirring, methanol (approximately 400 mi) is added to the resulting solution causing an immediate precipitation of an off-white solid. After stirring 15 minutes, the solid is filtered, washed with methanol, then ether and dried under high vacuum to yield approximately 57 gram product I.

To a mixture of product I (26 gram) in 360 mL THF containing 19 mL acetic acid at room temperature is rapidly added a solution of tetrabutylammonium fluoride hydrate (32 gram) in 640 mL THF. The reaction is stirred for 24 hours and concentrated to dryness in vacuo. The residue is dissolved in dichloromethane (400 mL), extracted twice with water, washed with brine, dried over sodium sulfate, filtered and concentrated to approximately 250 mL. The solution is diluted with an equal volume of diethyl ether to precipitate the product which is collected by filtration and air-dried to yield approximately 18 gram of product II.

To a solution of II (5.2 gram) in 500 mL dichloromethane at 0° C. is added 0.76 mL water and bis(triphenylphosphine)palladium (II) chloride (0.13 gram) followed by the rapid addition of tributyltin hydride (2.8 mi). The solution is stirred for 35 minutes at 0° C., then cooled to −7° C. to −10° C. Sodium 2-ethylhexanoate (2.6 gram) in 250 mL THF is then added dropwise over 30 minutes. The mixture is stirred an additional 15 minutes and the precipitated product is collected by filtration. The crude solid is stirred in 60 mL acetone for one hour, collected by centrifugation and dried in vacuo to yield 5 gram of the title compound.

The following QLAs are also prepared, according to the procedure of the above Example, with substantially similar results.

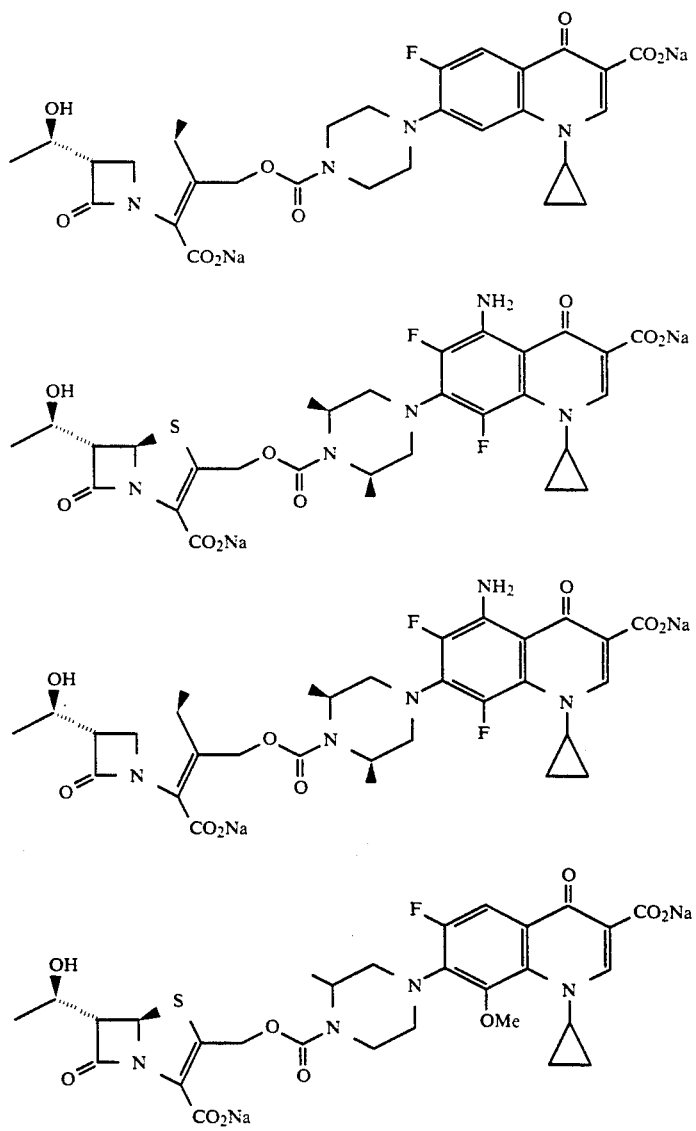

-continued
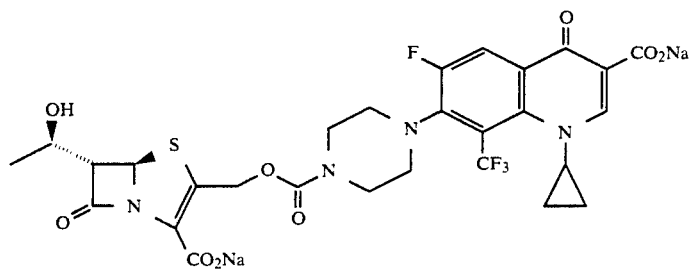
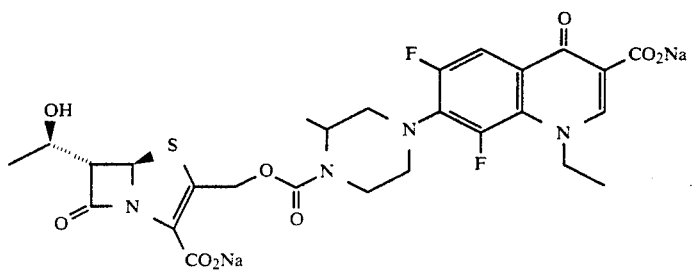
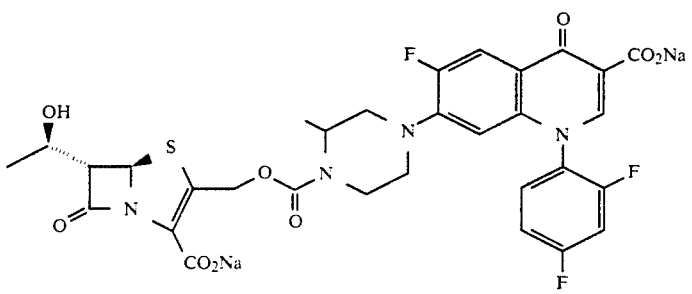
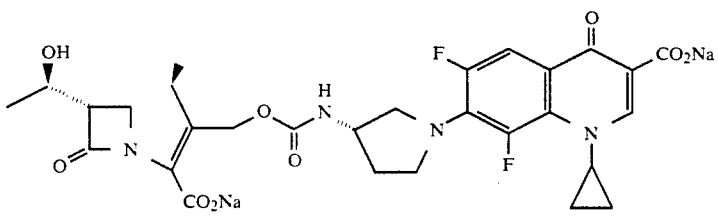
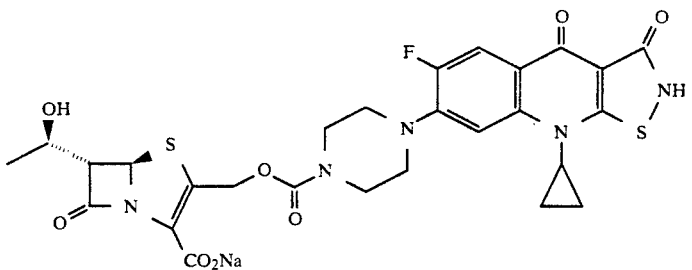
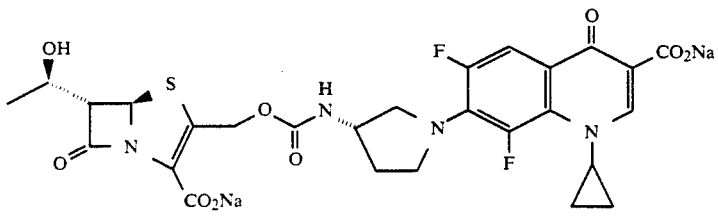

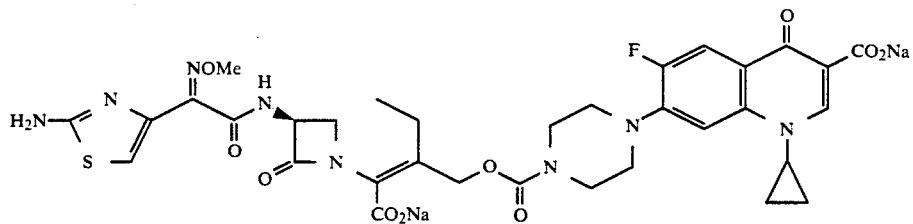
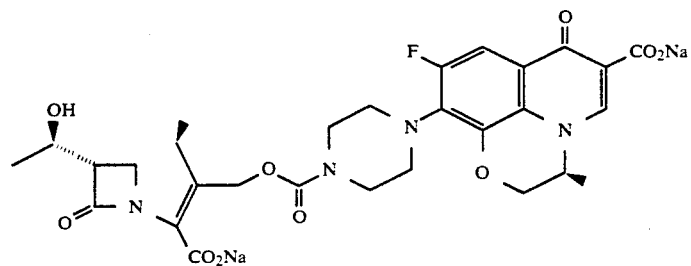
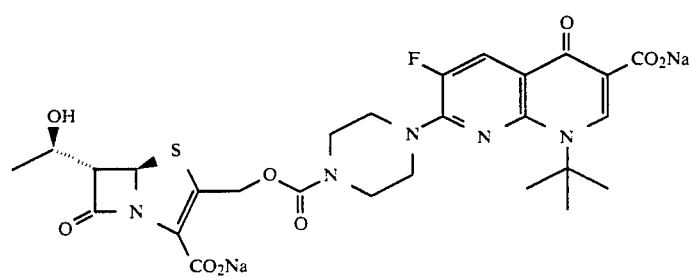
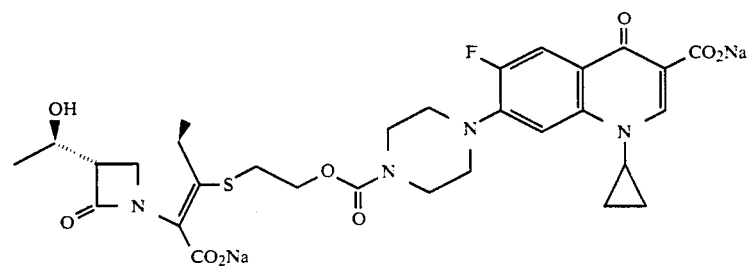
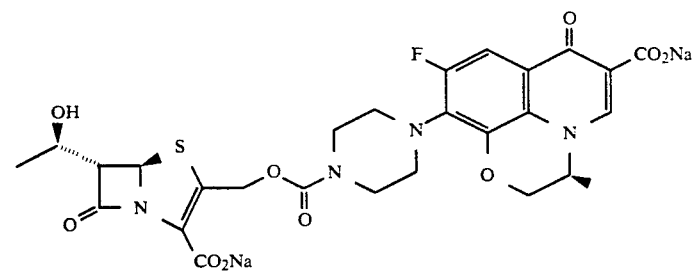

EXAMPLE 2

Preparation of
[5R-[5a,6a]]-[[[1-(3-Carboxy-1-(3,4-difluorophenyl)-6-fluoro-1,4-dihydro-4-oxo-1,8-naphthyridin-7-yl)-pyrrolidin-3-yl]amino]carbonyloxy]methyl]-6-[(R)-1-hydroxyethyl]-7-oxo-4-thia-1-azabicyclo[3.2.0]hept-2-ene-2-carboxylic Acid Disodium Salt

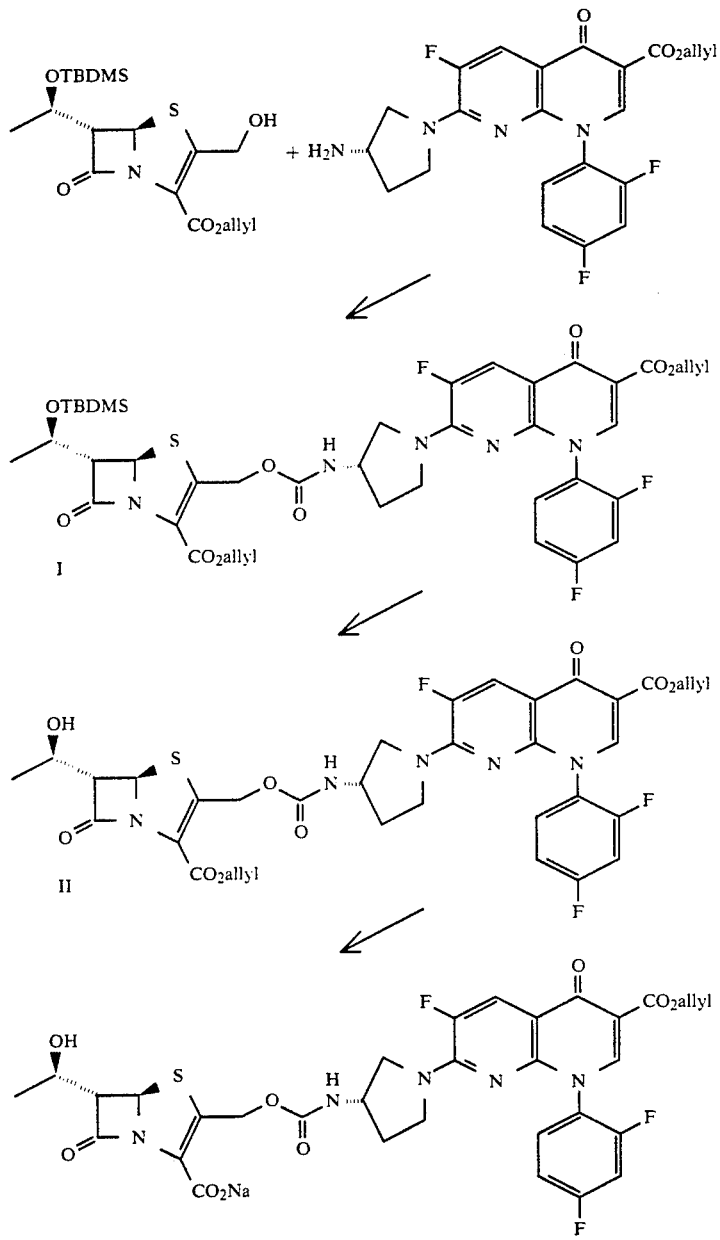

To a solution of 20% phosgene in toluene (1.3 mL) in 11 mL dichloromethane with diisopropylethylamine (0.48 mL) at −35° C. to −45° C. under a nitrogen atmsophere is added dropwise a solution of [5R-[4b,5a,6a,]]-6-[(R)-1-(t-butyldimethylsilyl-oxy)ethyl]-3-hydroxymethyl-4-methyl-7-oxo-1-azabicyclo[3.2.0-]hept-2-ene-2-carboxylic acid allyl ester (1.0 gram) in 11 mL dichloromethane. The reaction is stirred 1 hour at −35° C. to −45° C., then cooled to −78° C. A chilled (−40° C.) solution of the 7-(3-aminopyrrolidin-1-yl)-1-(2,4difluorophenyl)-6-fluoro-1,4-dihydro-4-oxo-1,8-naphthyridine-3-carboxylic acid allyl ester (1.1 gram) with diisopropylethylamine (0.48 mi) in 23 mL dichloromethane is added by cannula while maintaining the solution temperature below −70° C. After 30 min. the reaction mixture is extracted with cold 0.1N HCl and water. The dichloromethane layer is dried over sodium sulfate and the solvent evaporated under vacuum. The residue was triturated with hexanes to yield approximately 1.8 gram of product I.

To a room temperature solution of product I (2.2 gram) in 40 mL of THF with 1.4 mL of acetic acid is added tetrabutylammonium fluoride hydrate (2.3 gram) in 17 mL of THF dropwise. The mixture is stirred for 24 hours at room temperature under nitrogen atmosphere. The solvent is evaporated under vacuum, the residue is taken up in 50 mL dichloromethane and is washed with water and brine. The dichloromethane layer is dried over sodium sulfate and evaporated in vacuo. The residue is triturated with hexanes and the solid filtered, ground by mortar and pestle in ether, and then further triturated with ether. The solid is filtered to yield 0.80 gram of product II.

To a solution of product II (0.5 gram) in 40 mL of dichloromethane with bis(triphenylphosphine) palladium(II) chloride (0.019 gram) and 0.060 mL of water at 0° C. under a nitrogen atmosphere is added tributyltin hydride (0.46 ml) and the mixture allowed to stir for 30 min. Sodium 2-ethylhexanoate (0.22 gram) in 9.5 mL of THF is added to the above mixture at 0° C. very slowly over 20 min. and stirred for an additional 15 min. after the addition is completed. The precipitate is filtered and washed with ether and acetone. The solid is ground by mortar and pestle with acetone and further triturated with acetone. The solid is filtered and triturated with a 1:12 mixture of aqueous isopropanol. The solid is filtered to yield 0.22 gram the title compound.

The following QLAs are also prepared, according to the procedure of the above Example, with substantially similar results.

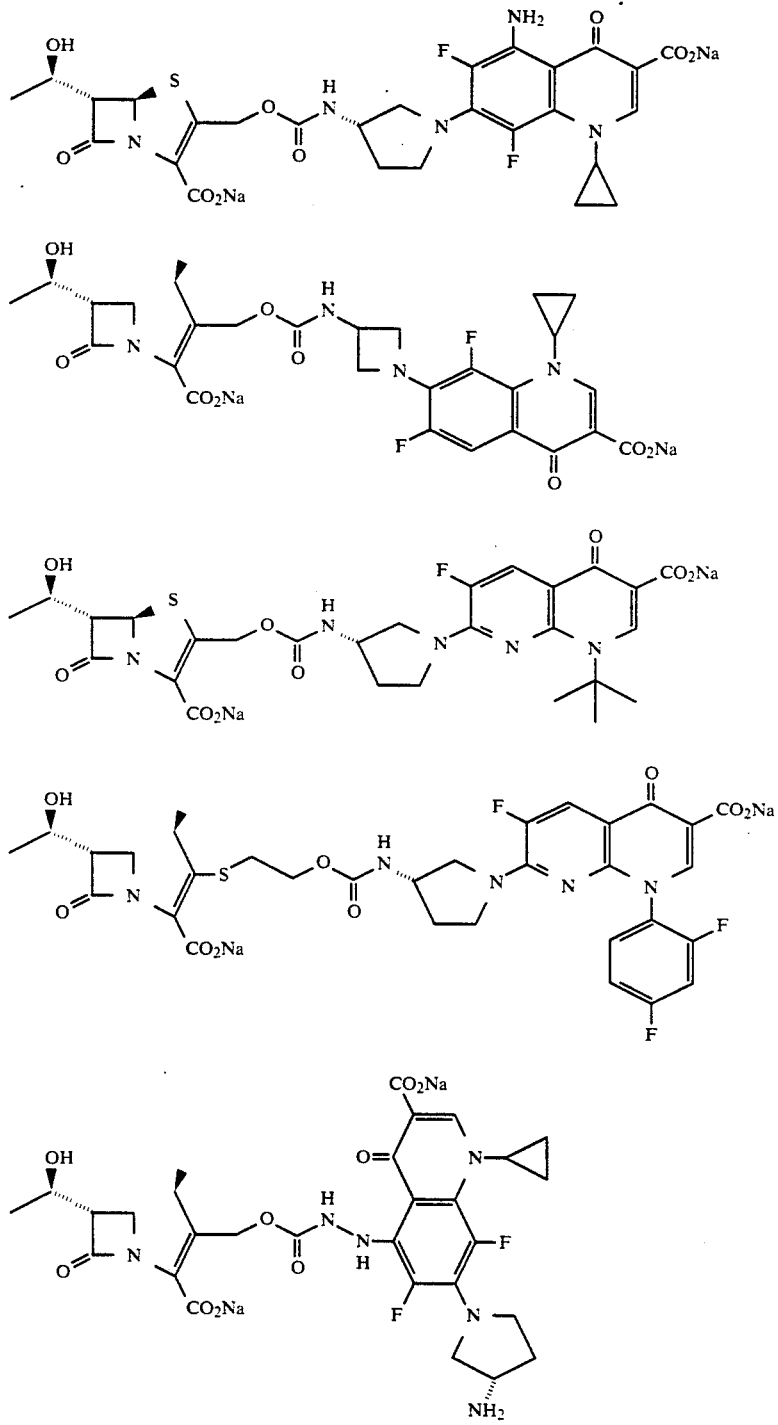

-continued
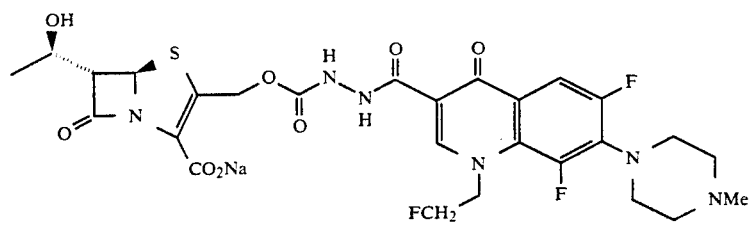
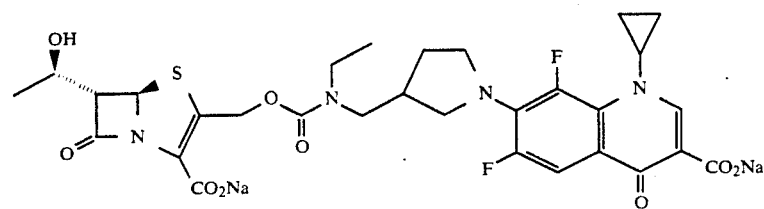
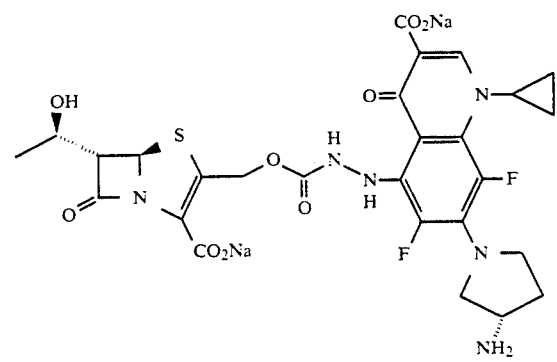
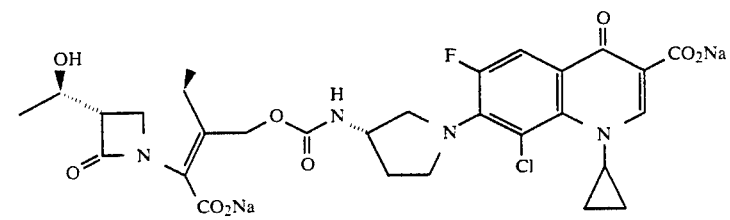
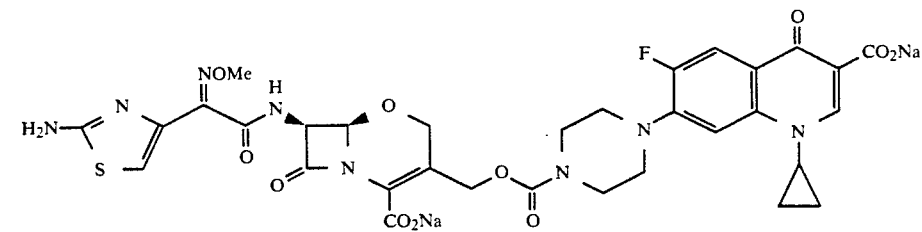
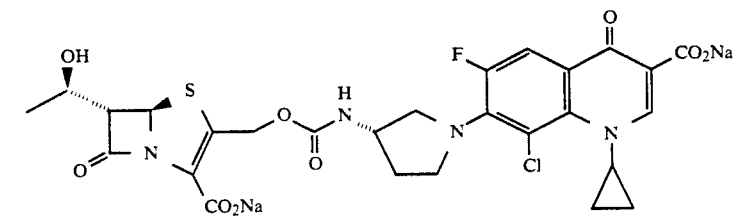

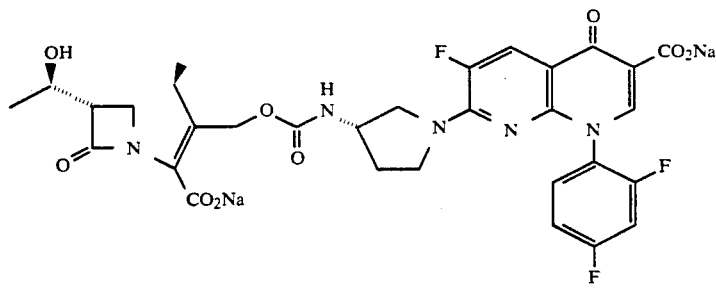
EXAMPLE 3
Preparation of
[5R-[4b,5a,6a]]-3-[[[4-(3-Carboxy-1-cyclopropyl-6-fluoro-1,4-dihydro-4-oxo-7-quinolinyl)-6-[(R)-1-hydroxyoxyethyl]-1-piperazinyl]carbonyloxy]methyl]-4-methyl-7-oxo-1-azabicyclo[3.2.0]hept-2-ene-2-carboxylic Acid Disodium Salt
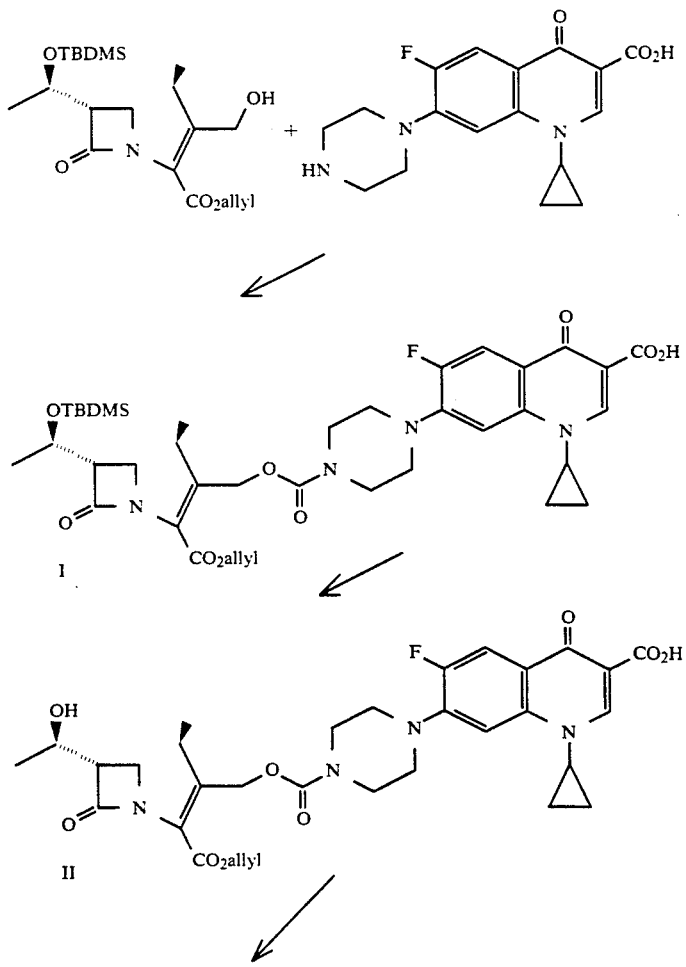

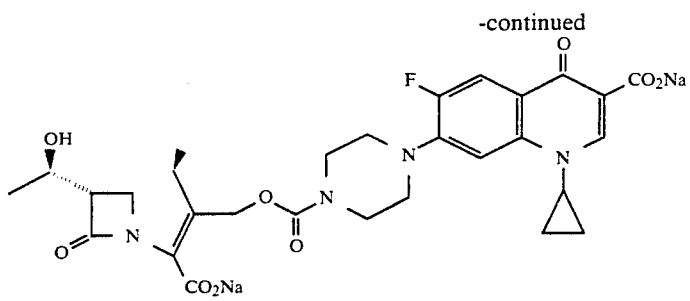

A 30 L reactor is fitted with a low temperature thermometer, overhead stirrer is charged with dichloromethane (6 L) and toluene (1.8 L) and cooled to −78° C. (internal temperature). Phosgene gas is introduced keeping the temperature below approximately −60° C. After recooling the mixture to −78° C., a solution of [5R-[4b,5a,6a]]-6-[(R)-1-(t-butyldimethylsilyloxy)ethyl]-3-hydroxymethyl-4-methyl-7-oxo-1-azabicyclo[3.2.0-]hept-2-ene-2-carboxylic acid allyl ester (1.2 kg) and N,N-diisopropylethylamine (580 mi) in 4.5 L dichloromethane is added to the reaction via metering pump at such a rate as to maintain the solution temperature between −75° C. and −70° C. A premixed solution of N-methyl-N-trimethylsilyl-trifluoroacetamide (1.7 L) and 1-cyclopropyl-6-fluoro-1,4-dihydro-4-oxo-7-(1-piperazinyl)-3-quinoline carboxylic acid (1 kg) in 7.5 L dichloromethane is then added to the reaction mixture at such a rate as to maintain the reaction temperature between −75° C. and −70° C. The reaction mixture is stirred for approximately 15 minutes and 1.5 L of water is added, allowing the solution to warm to approximately −10° C. A second aliquot of water (1.5 L) is added and the mixture is further warmed to approximately 10° C. The solution is filtered, extracted with water, washed with brine, dried over sodium sulfate and concentrated to approximately 6 L volume. With overhead stirring, methanol (3.2 L) is added to the resulting solution causing an immediate off-white precipitate. After stirring 15 minutes, the solid is filtered, washed with methanol, then ether and dried to yield approximately 2.1 kg product I.

A 30 L reactor is charged with THF (5.3 L), tetrabutylammonium fluoride (3.22 L, 1 M in THF) and acetic acid (790 mL). Solid product I (870 gram) is added at room temperature with overhead stirring and the resulting suspension is stirred under nitrogen for 20-24 hours. The reaction mixture becomes homogenous overnight. Water (20 L) is added to the reactor, the resulting suspension stirred for one hour, and then the product is filtered. The crude product is placed into the 30 L reactor, more water (20 L) is added, the suspension is stirred for 1 h, and then the product is refiltered, washed with THF (5 L), and then dried to give approximately 550 gram of product II.

A 30 L reactor equipped with an overhead stirrer is charged with product II (200 gram) and dichloromethane (12 L). The flask is purged with nitrogen and tetrakis(triphenyl-phosphine)palladium(O) (18 g) is added. The reaction mixture is cooled to −5° C. and a solution of sodium 2-ethylhexanoate (103 g) in THF (6 L) is slowly added to the reaction vessel via a metering pump at such a rate that the internal temperature was maintained between −5° C. to 0° C. Stirring of the reaction mixture is continued at −5° C. for another 1.5 hour after completion of addition. The reaction mixture is then centrifuged, the supernatant decanted off, and the product washed with additional dichloromethane (6 L). Following centrifugation and decantation, the product is then washed with additional dichloromethane (6 L). This process of washing, centrifugation, and decantation is repeated twice more. Following the final decantation step, final drying of the product affords 180 grams of the title compound.

What is claimed is:

1. A process for making an antimicrobial compound of the formula

[Q-L$^1$]-L-[L$^2$-B]

wherein (I) is a structure according to Formula (I)

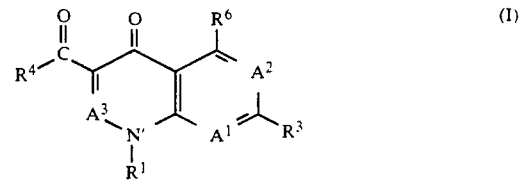

wherein (A) (1) A$^1$ is N or C(R$^7$); where
   (i) R$^7$ is hydrogen, hydroxy, alkoxy, nitro, cyano, halogen, alkyl, or N(R$^8$)(R$^9$), and
   (ii) R$^8$ and R$^9$ are, independently, R$^{8a}$ where R$^{8a}$ is hydrogen, alkyl, alkenyl, carbocyclic ring, or heterocyclic ring; or R$^8$ and R$^9$ together comprise a heterocyclic ring including the nitrogen to which they are bonded;

(2) A$^2$ is N or C(R$^2$); where R$^2$ is hydrogen or halogen;

(3) A$^3$ is N or C(R$^5$); where R$^5$ is hydrogen;

(4) R$^1$ is hydrogen, alkyl, a carbocyclic ring, a heterocyclic ring, alkoxy, hydroxy, alkenyl, arylalkyl, or N(R$^8$)(R$^9$);

(5) R$^3$ is hydrogen, halogen, alkyl, a carbocyclic ring, or a heterocyclic ring;

(6) R$^4$ is hydroxy; and (7) R$^6$ is hydrogen, halogen, nitro or N(R$^8$)(R$^9$);

(B) except that (1) when A$^1$ is C(R$^7$), R$^1$ and R$^7$ may together comprise a heterocyclic ring including N' and A$^1$;

(2) when A$^2$ is C(R$^2$), R$^2$ and R$^3$ may together comprise —O—(CH$_2$)$_n$—O—, where n is an integer from 1 to 4;

(3) when A$^3$ is C(R$^5$), R$^4$ and R$^5$ may together comprise a heterocyclic ring including the carbon atoms to which R$^4$ and R$^5$ are bonded and the carbon atom of Formula (I) to which said carbon atoms are bonded; and (4) when $A^3$ is $C(R^5)$, $R^1$ and $R^5$ may together comprise a heterocyclic ring including N' and the adjacent carbon to which $R^5$ is bonded;

(C) and except that one of $R^1$, $R^6$, or $R^3$ must be nil;

(II) B is a structure according to Formula (II):

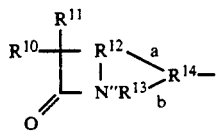
(II)

wherein (A) $R^{10}$ is hydrogen, halogen, alkyl, alkenyl, heteroalkyl, a carbocyclic ring, a heterocyclic ring, $R^{8a}$—O—, $R^{8a}$CH=N—, $(R^8)(R^9)$N—, $R^{17}$—C(=CHR$^{20}$)—C(=O)NH—, $R^{17}$—C(—NO—R$^{19}$)—C(=O)NH—, or $R^{18}$—(CH$_2$)$_m$—(=O)NH—; where (1) m is an integer from 0 to 9;

(2) $R^{17}$ is hydrogen, alkyl, alkenyl, heteroalkyl, heteroalkenyl, a carbocyclic ring, or a heterocyclic ring;

(3) $R^{18}$ is $R^{17}$, —$Y^1$, or —CH($Y^2$)($R^{17}$);

(4) $R^{19}$ is $R^{17}$, arylalkyl, herteroarylaklyl, —C($R^{22}$)($R^{23}$)COOH, —C(=O)O—$R^{17}$, or —C(=O)NH—$R^{17}$, where $R^{22}$ and $R^{23}$ are, independently, $R^{17}$ or together comprise a carbocyclic ring or a heterocyclic ring including the carbon atom to which $R^{22}$ and $R^{23}$ are bonded;

(5) $R^{20}$ is $R^{19}$, halogen, —$Y^1$, or —CH($Y^2$)($R^{17}$);

(6) $Y^1$ is —C(=O)$R^{21}$, —C(=O)$R^{21}$, —N($R^{24}$)$R^{21}$, —S(O)$_p R^{29}$, or —OR$^{29}$; and $Y^2$ is $Y^1$ or —OH, —SH, or —SO$_3$H;

(a) p is an integer from 0 to 2;

(b) $R^{24}$ is hydrogen; alkyl; alkenyl; heteroalkyl heteroalkenyl; a carbocyclic ring; a heterocyclic ring; —SO$_3$H; —C(=O)$R^{25}$; or, when $R^{18}$ is —CH(N($R^{24}$)$R^{21}$)($R^{17}$), $R^{24}$ may comprise a moiety bonded to $R^{21}$ to form a heterocyclic ring; and (c) $R^{25}$ is $R^{17}$, NH($R^{17}$), N($R^{17}$)($R^{26}$), O($R^{26}$), or S($R^{26}$); where $R^{26}$ is alkyl, alkenyl, a carbocyclic ring, a heterocyclic ring, or when $R^{25}$ is N($R^{17}$)($R^{26}$), $R^{26}$ may be a moiety bonded to $R^{17}$ to form a heterocyclic ring; and (7) $R^{21}$ is $R^{29}$ or hydrogen; where $R^{29}$ is alkyl; alkenyl; arylalkyl; heteroalkyl; heteroarylalkyl; a carbocyclic ring; a heterocyclic ring; or, when Y is N($R^{24}$)$R^{21}$ and $R^{21}$ is $R^{29}$, $R^{21}$ and $R^{24}$ may together comprise a heterocyclic ring including the nitrogen atom to which $R^{24}$ is bonded;

(B) $R^{11}$ is hydrogen, halogen, alkoxy, or $R^{27}$C(=O)NH—, where $R^{27}$ is hydrogen or alkyl;

(C) bond "a" is a single bond or is nil; and bond "b" is a single bond, a double bond, or is nil; except bond "a" and bond "b" are not both nil;

(D) $R^{12}$ is —C($R^{8a}$)—, or —CH$_2$—$R^{28}$—; where $R^{28}$ is —C($R^{8a}$), —O—, or —N—, and $R^{28}$ is directly bonded to N" in Formula (II) to form a 5-membered ring; except, if bond "a" is nil, then $R^{12}$ is (1) —C($R^{8a}$)($X^1$)—, where (i) $X^1$ is —$R^{21}$; —OR$^{30}$; —S(O)$_r R^{30}$, where r is an integer from 0 to 2; —OC=O)R$^{30}$; or N($R^{30}$)$R^{31}$; and (ii) $R^{30}$ and $R^{31}$ are, independently, alkyl, alkenyl, carbocyclic ring or heterocyclic ring substituents; or $R^{30}$ and $R^{31}$ together comprise a heterocyclic ring including the nitrogen atom to which $R^{30}$ and $R^{31}$ are bonded; or (2) —CH$_2$-$R^{32}$—; where $R^{32}$ is —C($R^{8a}$)($R^{21}$), —O—, or —NR$^{8a}$, and $R^{32}$ is directly bonded to N" in Formula (II) to form a 5-membered ring;

(E) (1) if bond "b" is a single bond, $R^{13}$ is —CH($R^{33}$)—; or, —C(O)NHSO$_2$—, if bond "a" is nil; or —CI($R^{33}$)— if $R^{14}$ contains a $R^{36}$ moiety; where $R^{33}$ is hydrogen or COOH, and C* is linked to $R^{36}$ to form a 3-membered ring;

(2) if bond "b" is a double bond, $R^{13}$ is —C($R^{33}$)=; or (3) if bond "b" is nil, $R^{13}$ is hydrogen, —SO$_3$H, —PO(OR$^{34}$)OH, —C(O)NHSO$_2$N($R^{34}$)($R^{35}$), —OSO$_3$H, —CH($R^{35}$)COOH, or —OCH($R^{34}$)COOH; where $R^{34}$ is hydrogen, alkyl, alkenyl, a carbocyclic ring, or a heterocyclic ring; and $R^{35}$ is hydrogen, alkyl, alkenyl, or —NHR$^{8a}$; or, if $R^{13}$ is —C(O)NHSO$_2$N($R^{34}$)($R^{35}$), $R^{34}$ and $R^{35}$ may together comprise a heterocyclic ring including the nitrogen to which $R^{34}$ and $R^{35}$ are bonded; and (F) (1) if bond "a" or bond "b" is nil, then $R^{14}$ is nil;

(2) if bond "a" and "b" are single bonds, $R^{14}$ is —W—C'''=C($R^{8a}$)—$R^{37}$—, or —W—C'''($R^{36}$)—$R^{37}$—; or (3) if bond "a" is a single bond and bond "b" is a double bond, $R^{14}$ is —C($R^{8a}$)($R^{38}$)—W—C'''—$R^{37}$—, —W'—C($R^{8a}$)($R^{38}$)—C'''—$R^{37}$—; or —W—C'''—$R^{37}$—; where (a) W is O; S(O)s, where s is an integer from 0 to 2; or C($R^{38}$), where $R^{38}$ is hydrogen, alkyl or alkoxy;

(b) W' is O; or C($R^{38}$);

(c) $R^{36}$ hydrogen; alkyl; alkenyl; —COOH; or, if $R^{13}$ is —C*($R^{33}$), $R^{36}$ may be linked to C* to form a 3-membered carbocyclic ring;

(d) $R^{37}$ and is nil, alkyl, alkenyl, a carbocyclic ring, or a heterocyclic ring; and (e) C''' is directly bonded to $R^{13}$ to form a 5- or 6-membered ring; and (III)(A) L is —C(=O)—, and is bonded to $L^3$ and $L^4$ (B) $L^1$ is $L^3$ or $R^{15}L^3$; where (1) $L^3$ is nitrogen;

(2) $R^{15}$ is alkyl, alkenyl, heteroalkyl, a heterocyclic ring, a carbocyclic ring, or $R^{15}$ together with $L^3$ is a heteroalkyl or a heterocyclic ring; and (3) $L^1$ is bonded to Q at the point of attachment of $R^1$, $R^6$ or $R^3$, whichever is nil;

(C) $L^2$ is $L^4$, —$X^2_r$—$R^{39}$—$L^4$, or $X^3_r$—$R^{39}$-$L^4$; where (1) $L^4$ is oxygen;

(2) $X^2$ is oxygen, or S(O)$_v$, where v is 0, 1, or 2;

(3) $X^3$ is nitrogen; N($R^{40}$); N+($R^{41}$)($R^{42}$); or $R^{43}$—N($R^{41}$); and is linked to $R^{14}$ by a single or double bond; or, if $R^{14}$ is nil, $X^3$ is linked to B by a single or double bond; where (a) $R^{40}$ is $R^{8a}$; —OR$^{8a}$; or —C(=O)R$^{8a}$;

(b) $R^{41}$ and $R^{42}$ are, independently, hydrogen; alkyl; alkenyl; carbocyclic rings; heterocyclic rings; or, if $R^6$ is $R^{16}X$, then $R^{41}$ and $R^{42}$ together with Q" may comprise a heterocyclic ring as $R^{16}$;

(c) $R^{43}$ is $N(R^{41})$, oxygen or sulfur;

(4) t is 0 or 1;

(5) $R^{39}$ is alkyl, alkenyl, heteroalkyl, heteroalkenyl, a carbocyclic ring, or a heterocyclic ring; and (6) (a) if bond "a" or bond "b" is nil, then $L^2$ is bonded directly to $R^{12}$ or $R^{13}$; or (b) if bond "a" and bond "b" are not nil, then $L^2$ is bonded to $R^{14}$;

and pharmaceutically-acceptable salts and biohydrolyzable esters thereof, and hydrates thereof; comprising the steps of:

(1) Reacting a lactam compound of the formula $B-L^4-H$ with phosgene to form an intermediate compound of the formula $B-L^4-C(=O)-Cl$; and (2) Coupling said intermediate compound with a quinolone compound of the formula $Q-L^3-R^{44}$; wherein $R^{44}$ is hydrogen, $Si(R^{45})_3$, or $Sn(R^{45})_3$; and $R^{45}$ is lower alkyl.

2. A process, according to claim 1, additionally comprising (a) a step, prior to said reacting step, wherein an ester of said lactam compound is formed;

(b) a step, prior to said coupling step, wherein an ester of said quinolone compound is formed; and (c) deprotection steps, after said coupling step, wherein said esters are removed.

3. A process, according to claim 1, wherein said coupling step comprises adding a solution containing said quinolone compound to a solution containing said intermediate compound.

4. A process, according to claim 3, wherein said solutions are in a halocarbon solvent.

5. A process, according to claim 4, wherein said halocarbon solvent is selected from the group consisting of methylene chloride, chloroform, dichloroethane, and mixtures thereof.

6. A process, according to claim 3, wherein said reacting step and said coupling step are performed at a temperature of from about $-80°$ C. to about $0°$ C.

7. A process, according to claim 6, wherein said temperature is from about $-80°$ C. to about $-40°$ C.

8. A process, according to claim 6, wherein $R^{44}$ is $Si(R^{45})_3$.

9. A process, according to claim 3, wherein $R^{14}$ is $-W-C'''-R^{37}-$.

10. A process, according to claim 9, wherein W is $S(O)_s$.

11. A process, according to claim 10, wherein $A^1$ is $C(R^7)$, $A^2$ is $C(R^2)$, and $A^3$ is $C(R^5)$; or $A^1$ is nitrogen, $A^2$ is $C(R^2)$, and $A^3$ is $C(R^5)$.

12. A process, according to claim 11, wherein $A^1$ is $C(R^7)$, $A^2$ is $C(R^2)$, and $A^3$ is $C(R^5)$.

13. A process, according to claim 11, wherein $R^3$ is nil and comprises a bond to $L^1$.

14. A process, according to claim 11, wherein $R^6$ is nil and comprises a bond to $L^1$.

15. A process, according to claim 11, wherein said quinolone compound is:

1-Cyclopropyl-6-fluoro-1,4-dihydro-4-oxo-7-piperazinyl-quinoline-3-carboxylic acid;

1-Cyclopropyl-6-fluoro-1,4-dihydro-4-oxo-7-piperazinyl-quinoline-3-carboxylic acid allyl ester;

1-Cyclopropyl-6-fluoro-1,4-dihydro-4-oxo-7-piperazinyl-quinoline-3-carboxylic acid diphenylmethyl ester;

1-Cyclopropyl-6-fluoro-1,4-dihydro-4-oxo-7-piperazinyl-quinoline-3-carboxylic acid t-butyl ester;

1-Cyclopropyl-6-fluoro-1,4-dihydro-4-oxo-7-piperazinyl-quinoline-3-carboxylic acid 2,2,2-trichloroethyl ester;

7-(3-Amino-1-pyrrolidinyl)-1-cyclopropyl-6,8-difluoro-1,4-dihydro-4-oxo-quinoline-3-carboxylic acid;

7-(3-Amino-1-pyrrolidinyl)-1-cyclopropyl-6,8-difluoro-1,4-dihydro-4-oxo-quinoline-3-carboxylic acid allyl ester;

7-(3-Amino-1-pyrrolidinyl)-1-cyclopropyl-6,8-difluoro-1,4-dihydro-4-oxo-quinoline-3-carboxylic acid allyl ester;

5-Amino-7-(3-amino-1-pyrrolidinyl)-1-cyclopropyl-6,8-difluoro-1,4-dihydro-4-oxo-quinoline-3-carboxylic acid allyl ester;

5-Amino-1-cyclopropyl-6,8-difluoro-1,4-dihydro-7-(2,6-dimethyl-4-piperazinyl)-4-oxo-quinoline-3-carboxylic acid;

7-(3-Amino-1-pyrrolidinyl)-1-(2,4-difluorophenyl)-6-fluoro-1,4-dihydro-4-oxo-1,8-naphthyridine-3-carboxylic acid allyl ester; or 7-[3-(t-Butyloxycarbonyl)amino-1-pyrrolidinyl]-1-cyclopropyl-6,8-difluoro-1,4-dihydro-5-hydrazino-4-oxo-quinoline-3-carboxylic acid allyl ester.

16. A process, according to claim 11, wherein lactam compound is:

[5R-[5a,6a]]-6-[(R)-1-(t-butyldimethylsilyloxy)ethyl]-3-hydroxymethyl-7-oxo-4-thia-1-azabicyclo[3.2.0]hept-2-ene-2-carboxylic acid allyl ester;

[5R-[5a,6a]]-6-[(R)-1-[(allyloxycarbonyl)oxy]ethyl]-3-hydroxymethyl-7-oxo-4-thia-1-azabicyclo[3.2.0]hept-2-ene-2-carboxylic acid allyl ester;

[5R-[5a,6a]]-6-[(R)-1-[(2,2,2-trichloroethyloxycarbonyl)oxy]ethyl]-3-hydroxymethyl-7-oxo-4-thia-1-azabicyclo[3.2.0]hept-2-ene-2-carboxylic acid 2,2,2-trichloroethyl ester;

[5R-[5a,6a]]-6-[(R)-1-(t-butyldimethylsilyloxy)ethyl]-3-hydroxymethyl-7-oxo-4-thia-1-azabicyclo[3.2.0]hept-2-ene-2-carboxylic acid diphenylmethyl ester;

[5R-[5a,6a]]-6-[(R)-1-(t-butyldimethylsilyloxy)ethyl]-3-hydroxymethyl-7-oxo-4-thia-1-azabicyclo[3.2.0]hept-2-ene-2-carboxylic acid t-butyl ester;

[5R-[4b,5a,6a]]-6-[(R)-1-(t-butyldimethylsilyloxy)ethyl]-3-hydroxymethyl-4-methyl-7-oxo-1-azabicyclo[3.2.0]hept-2-ene-2-carboxylic acid allyl ester;

[5R-[5a,6a]]-6-[(R)-1-(t-butyldimethylsilyloxy)ethyl]-3-(2-hydroxyethylthio)-7-oxo-4-thia-1-azabicyclo[3.2.0]hept-2-ene-2-carboxylic acid allyl ester; or

[5R-[4b,5a,6a]]-6-[(R)-1-(t-butyldimethylsilyloxy)ethyl]-3-(2-hydroxyethylthio)-4-methyl-7-oxo-1-azabicyclo[3.2.0]hept-2-ene-2-carboxylic acid allyl ester.

17. A process, according to claim 1, wherein said antimicrobial compound is:

[5R-[5a,6a]]-3-[[[4-(3-Carboxy-1-cyclopropyl-6-fluoro-1,4-dihydro-4-oxo-7-quinolinyl)-1-piperazinyl]carbonyloxy]methyl]-6-[(R)-1-hydroxyethyl]-7-oxo-4-thia-1-azabicyclo[3.2.0]hept-2-ene-2-carboxylic Acid, Disodium Salt;

[5R-[4b,5a,6a]]-3-[[[4-(3-Carboxy-1-cyclopropyl--6-fluoro-1,4-dihydro-4-oxo-7-quinolinyl)-1-piperazinyl]carbonyloxy]methyl]-6-[(R)-1-hydroxyethyl]-4-methyl-7-oxo-1-azabicyclo[3.2.0]hept-2-ene-2-carboxylic Acid, Disodium Salt;

[5R-[5a,6a]]-3-[[[[4-(3-Carboxy-1-cyclopropyl-6,8-difluoro-1,4-dihydro-4-oxo-7-quinolinyl)-(S)-3-pyrrolidinyl]amino]carbonyloxy]methyl]-6-[(R)-1-hydroxyethyl]-7-oxo-4-thia-1-azabicyclo[3.2.0]hept-2-ene-2-carboxylic Acid, Disodium Salt;

[5R-[4b,5a,6a]]-3-[[[[4-(3-Carboxy-1-cyclopropyl-6,8-difluoro-1,4-dihydro-4-oxo-7-quinolinyl)-(S)-3-pyrrolidinyl]amino]carbonyloxy]methyl]-6-[(R)-1-hydroxyethyl]-4-methyl-7-oxo-1-azabicyclo[3.2.0]hept-2-ene-2-carboxylic Acid, Disodium Salt;

[5R-[5a,6a]]-3-[[[[4-[3-Carboxy-1-(2,4-difluorophenyl)-6-fluoro-1,4-dihydro-4-oxo-1,8-naphthyridin-1-yl]-(S)-3-pyrrolidinyl]amino]-carbonyloxy]methyl]-6-[(R)-1-hydroxyethyl]-7-oxo-4-thia-1-azabicyclo[3.2.0]hept-2-ene-2-carboxylic Acid, Disodium Salt;

[5R-[4b,5a,6a]]-3-[[[[4-[3-Carboxy-1-(2,4-difluorophenyl)-6-fluoro-1,4-dihydro-4-oxo-1,8-naphthyridin-1-yl]-(S)-3-pyrrolidinyl]amino]-carbonyloxy]methyl]-6-[(R)-1-hydroxyethyl]-4-methyl-7-oxo-1-azabicyclo[3.2.0]hept-2-ene-2-carboxylic Acid, Disodium Salt;

[5R-[5a,6a]]-3-[[[4-(5-Amino-3-carboxy-1-cyclopropyl-6,8-difluoro-1,4-dihydro-4-oxo-7-quinolinyl)-2,6-dimethyl-4-piperazinyl]carbonyloxy]methyl]-6-[(R)-1-hydroxyethyl]-7-oxo-4-thia-1-azabicyclo[3.2.0]hept-2-ene-2-carboxylic Acid, Disodium Salt;

[5R-[4b,5a,6a]]-3-[[[4-(5-Amino-3-carboxy-1-cyclopropyl-6,8-difluoro-1,4-dihydro-4-oxo-7-quinolinyl)-2,6-dimethyl-4-piperazinyl]carbonyloxy]methyl]-6-[(R)-1-hydroxyethyl]-4-methyl-7-oxo-1-azabicyclo[3.2.0]hept-2-ene-2-carboxylic Acid, Disodium Salt;

[5R-[5a,6a]]-3-[[[2-[7-((S)-3-Amino-1-pyrrolidinyl)-3-carboxy-1-cyclopropyl-6,8-difluoro-1,4-dihydro-4-oxo-5-quinolinyl]-1-hydrazino]-carbonyloxy]methyl]-6-[(R)-1-hydroxyethyl]-7-oxo-4-thia-1-azabicyclo[3.2.0]hept-2-ene-2-carboxylic Acid, Disodium Salt; or

[5R-[4b,5a,6a]]-3-[[[2-[7-((S)-3-Amino-1-pyrrolidinyl)-3-carboxy-1-cyclopropyl-6,8-difluoro-1,4-dihydro-4-oxo-5-quinolinyl]-1-hydrazino]-carbonyloxy]methyl]-6-[(R)-1-hydroxyethyl]-4-methyl-7-oxo-1-azabicyclo[3.2.0]hept-2-ene-2-carboxylic Acid, Disodium Salt.

* * * * *

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

Col. 17, line 5 of the patent, "(b)", should read --(c)--.

Col. 20, line 10 of the patent, "(20mi)" should read --(20 mL)--.

Col. 20, line 16 of the patent, "(56 mi)" should read --(56 mL)--.

Col. 21, lline 13 of the patent, "400 mi" should read --400 mL)--.

Col. 22, line 12 of the patent, "(2.8 mi)" should read --(2.8 mL)--.

Signed and Sealed this

Fourth Day of June, 1996

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

6. Col. 22, first structure,

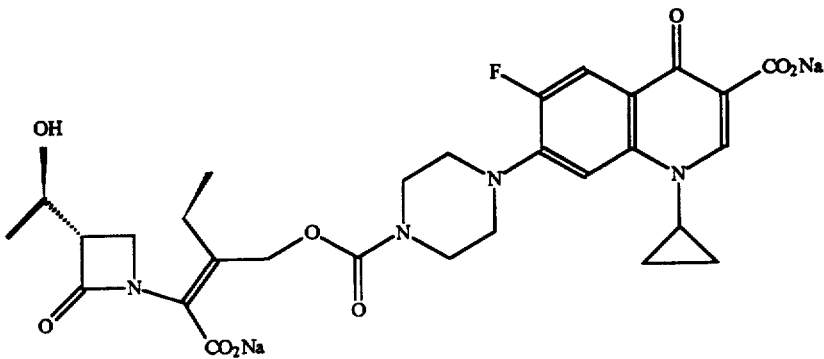

should read

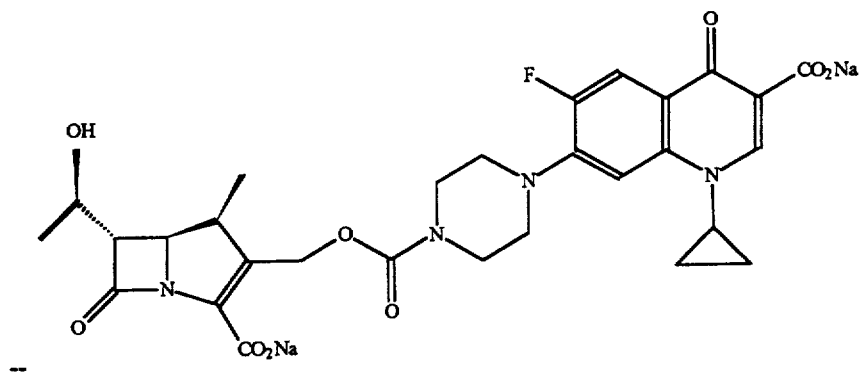

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

7. Col. 22, third structure,

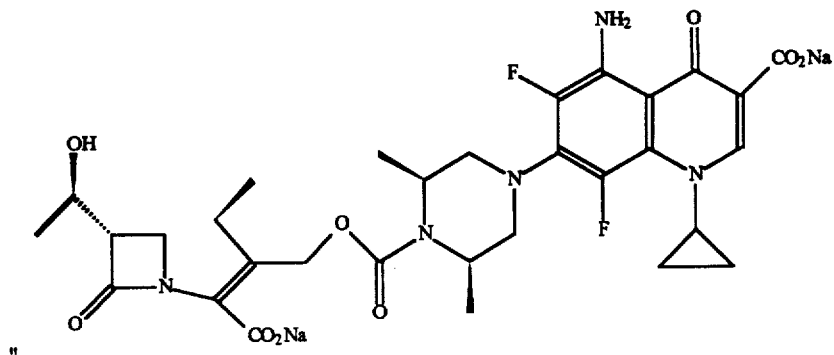

should read

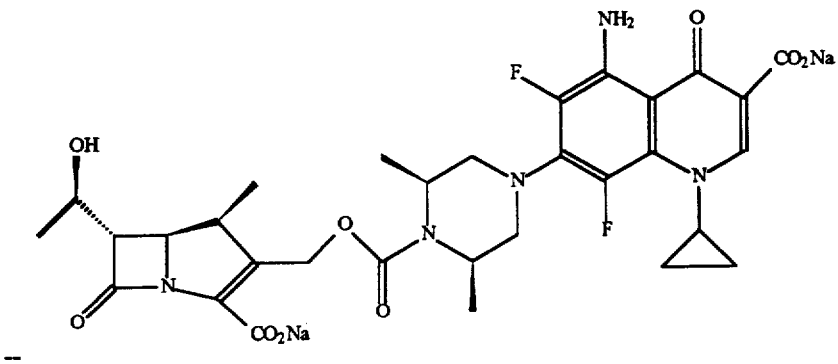

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

8. Col. 23, fourth structure,

"
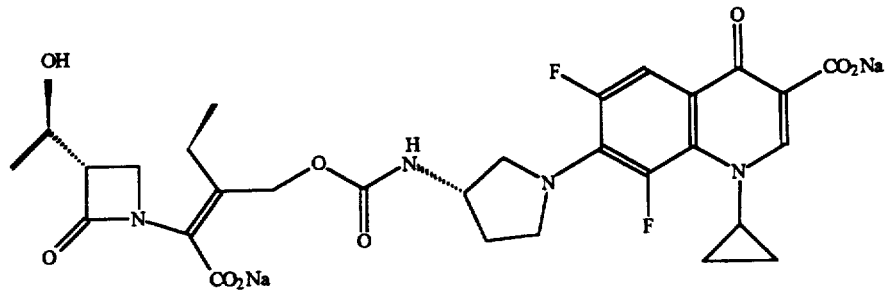
"

should read

--
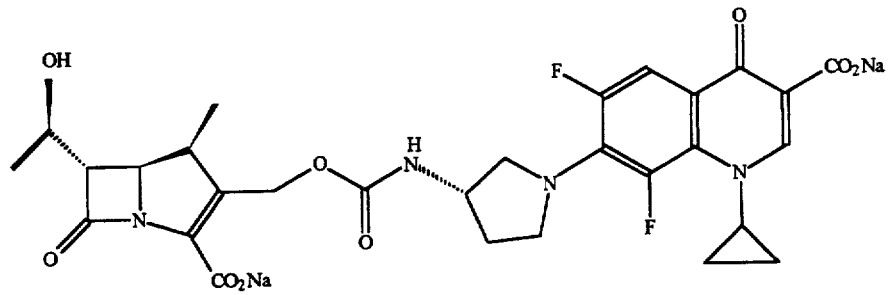
--.

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

9. Col. 25, first structure

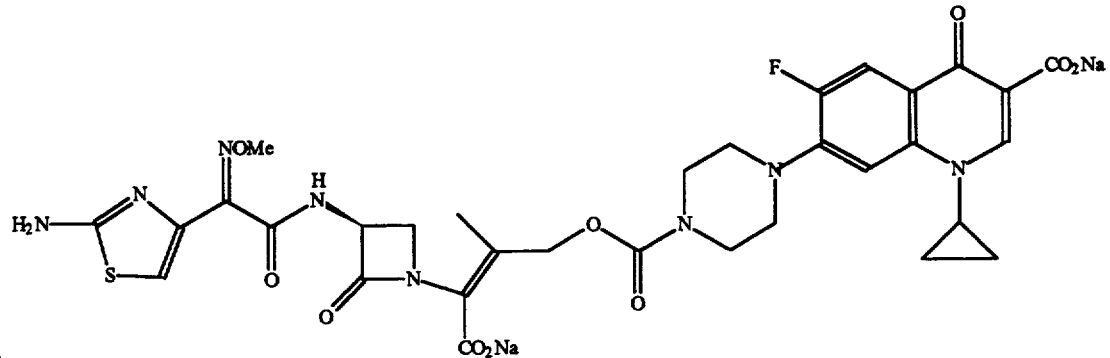

"

should read

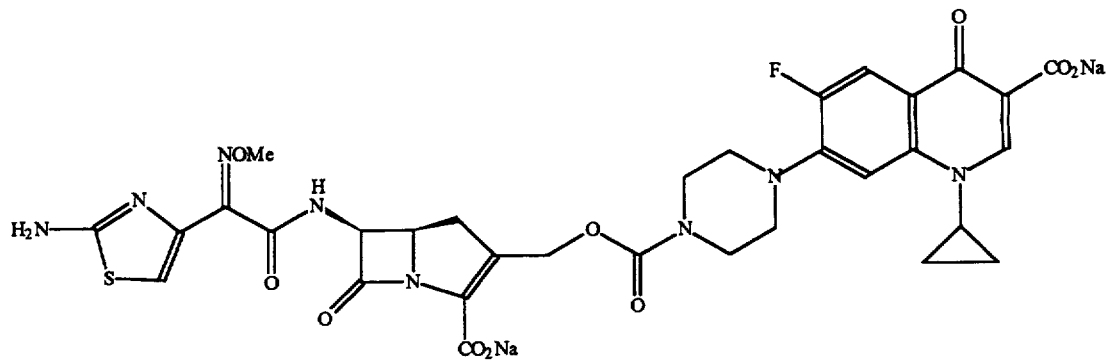

--

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

Page 6 of 18

It is certified that error appears in the above-identified patent and that said Letters Patent is hereby corrected as shown below:

10. Col. 25, second structure

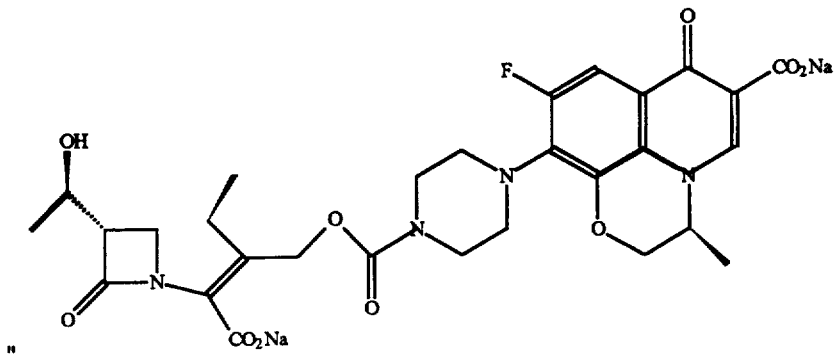

should read

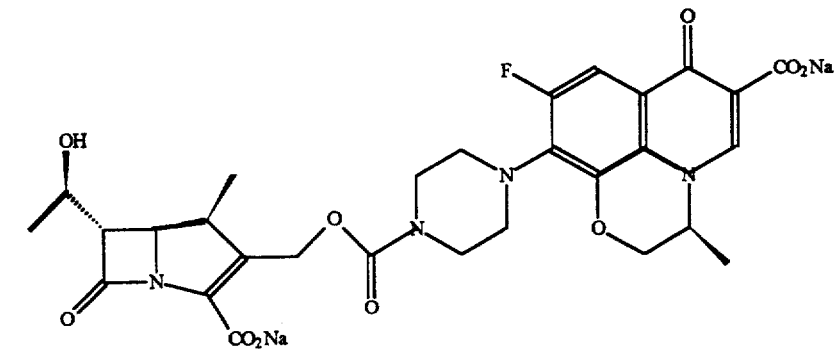

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

11. Col. 25, third structure

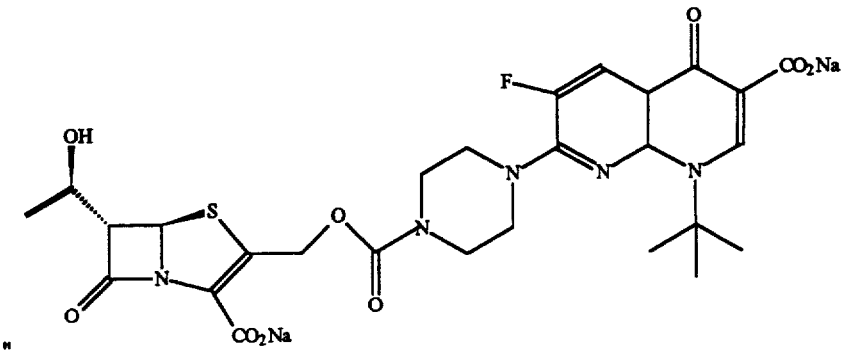

should read

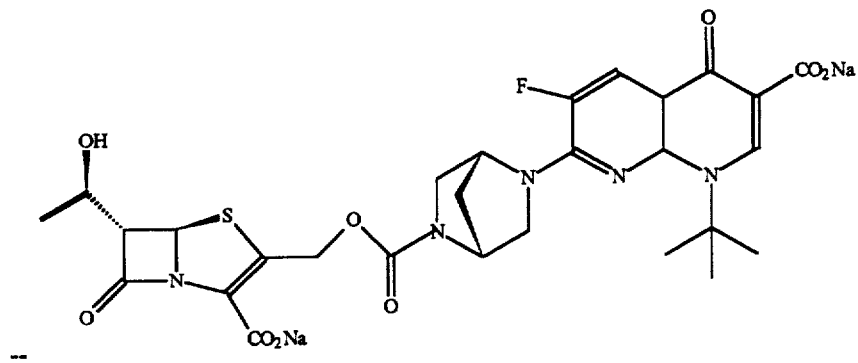

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

12. Col. 25, fourth structure

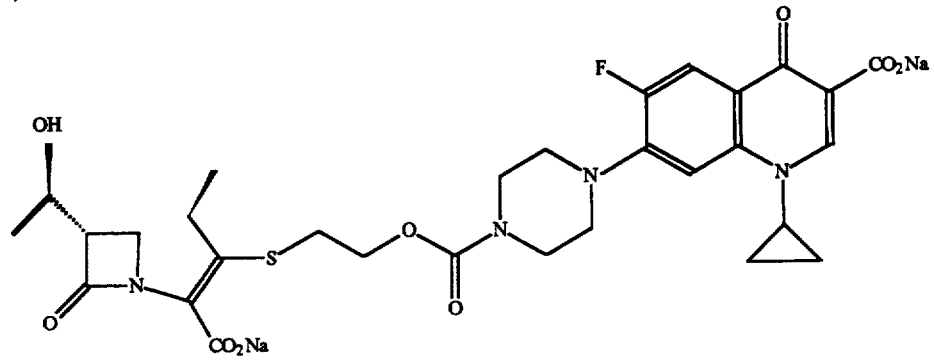

should read

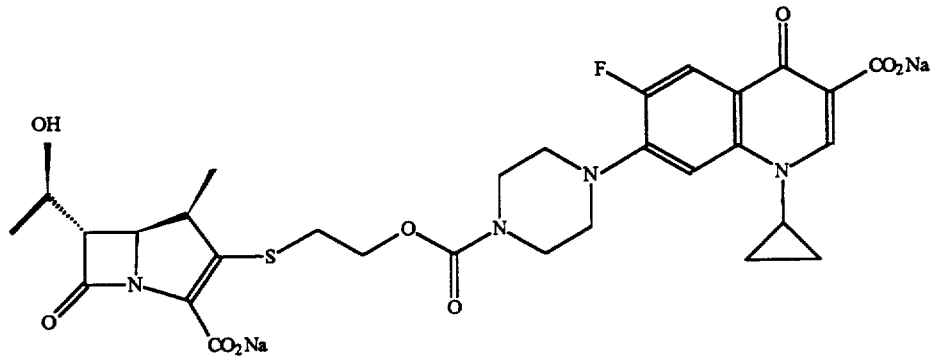

13. Col. 27, line 68 of the patent, "4difluorophenyl" should read --4-difluorophenyl--.

14. Col. 28, line 2 of the patent, "(0.48 mi)" should read --(0.48 mL)--.

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

15. Col. 27, fourth structure

"
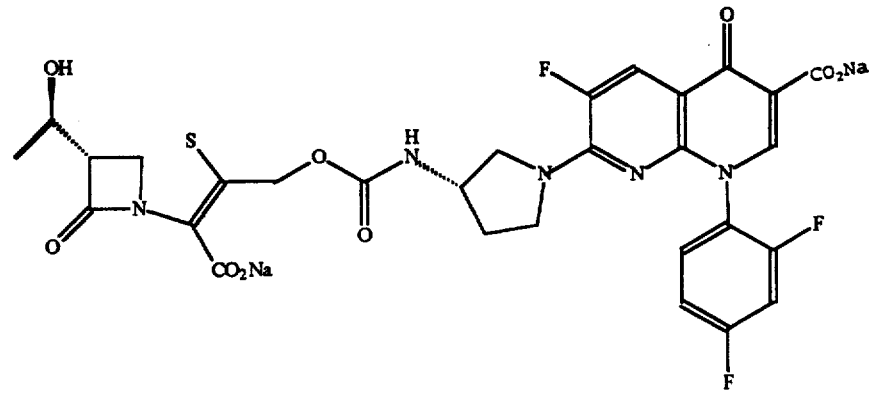
"

should read

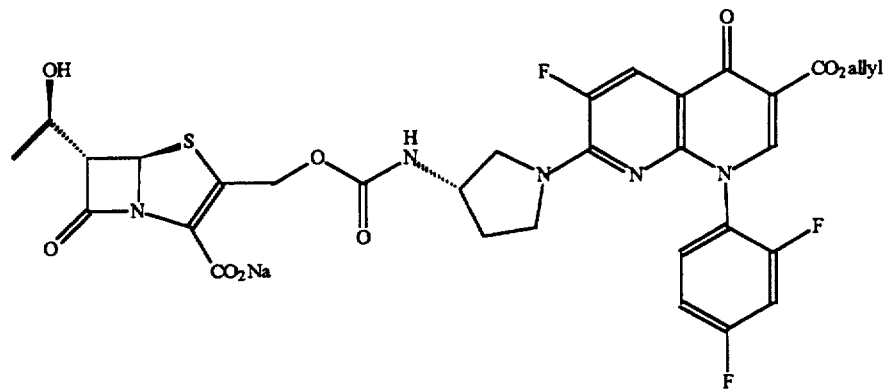
--.

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

16. Col. 29, line 9 of the patent, "(0.46 mi)" should read --(0.46 mL)--.

17. Col. 30, second structure

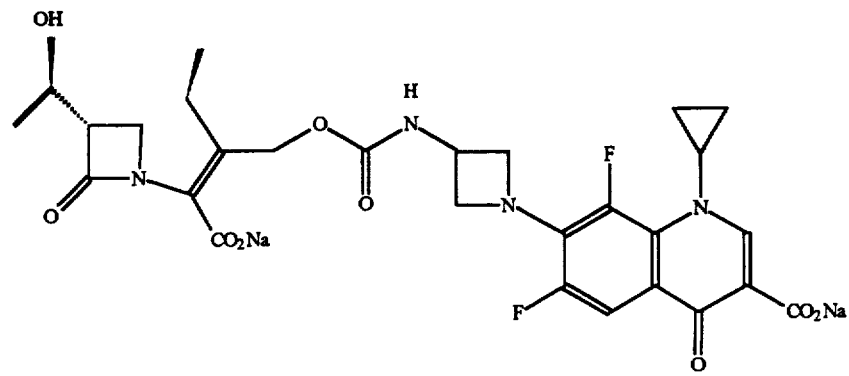

"

should read

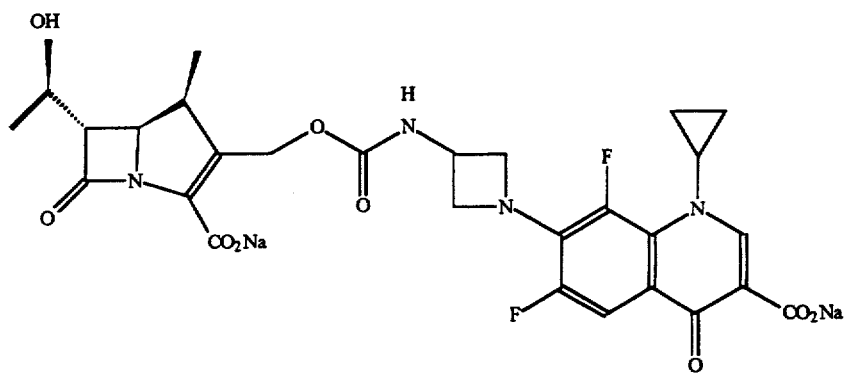

--.

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

18. Col. 30, fourth structure

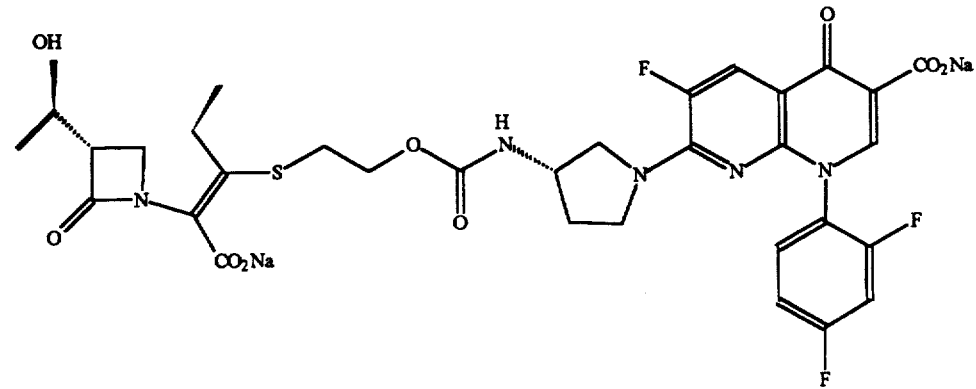

"

should read

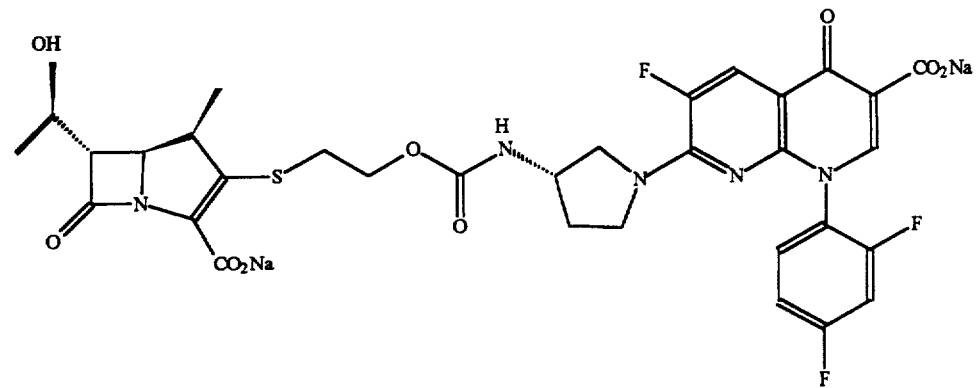

--.

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

19. Col. 30, fifth structure

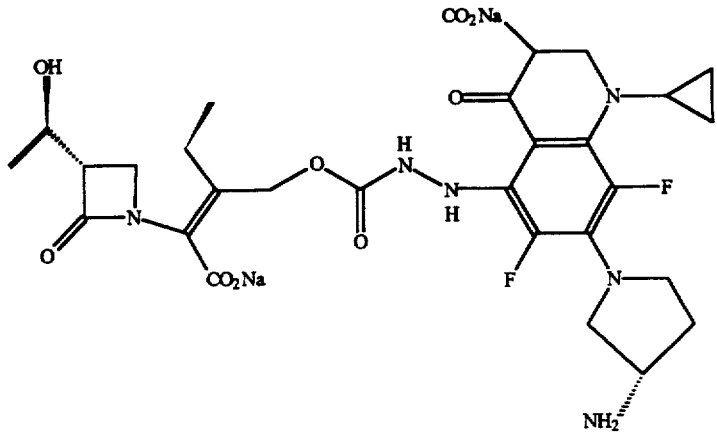

"

should read

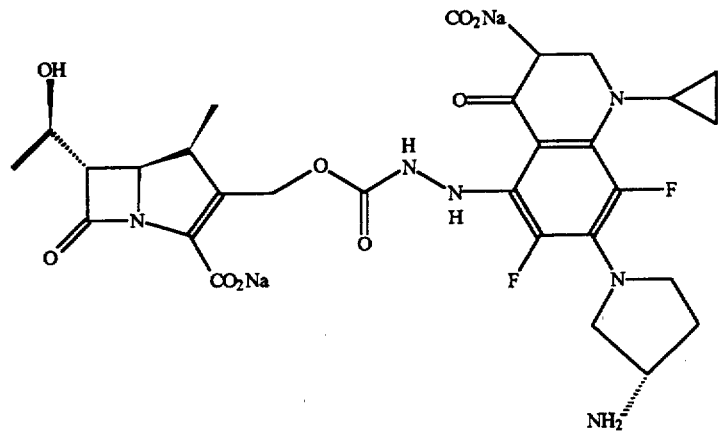

--.

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

20. Col. 31, fourth structure

"
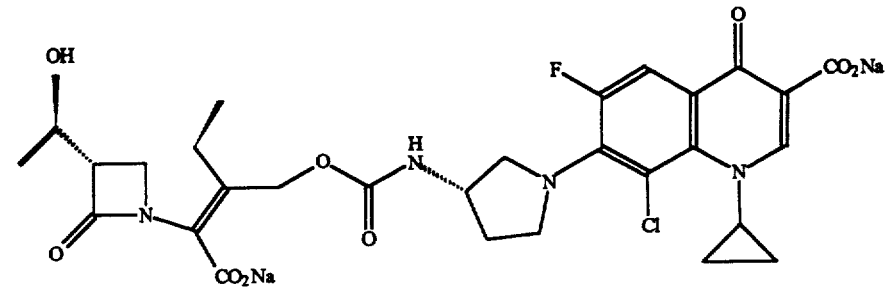
"

should read

--
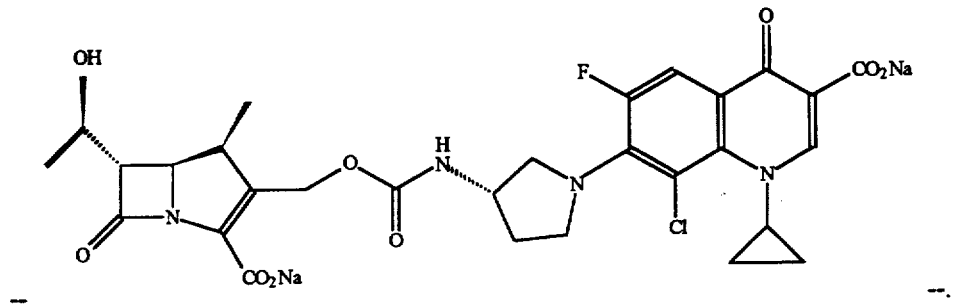
--.

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

21. Col. 33, first structure

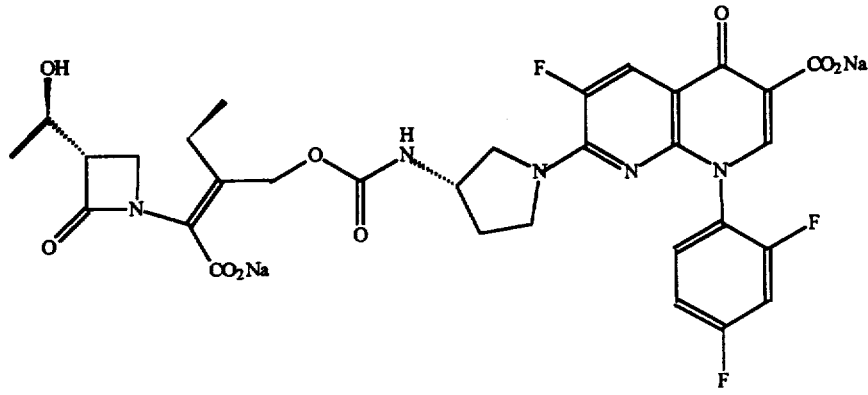

"

should read

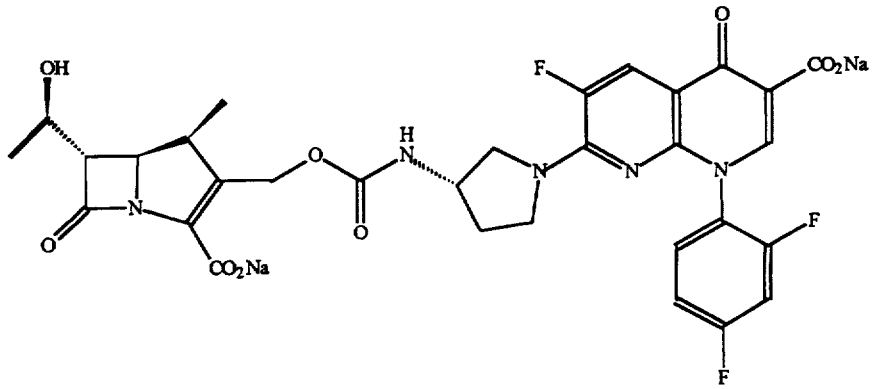

--.

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

22. Col. 34, first structure

"
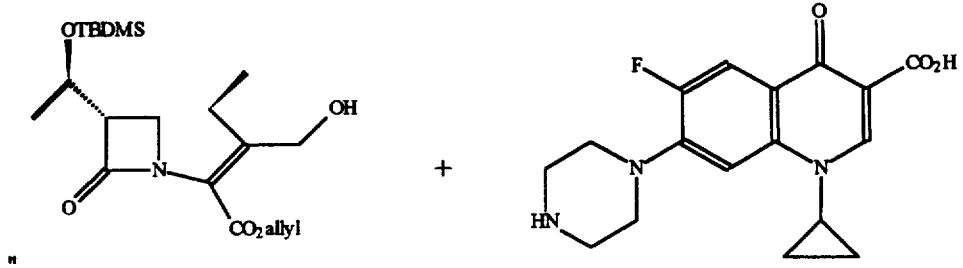
"

should read

--
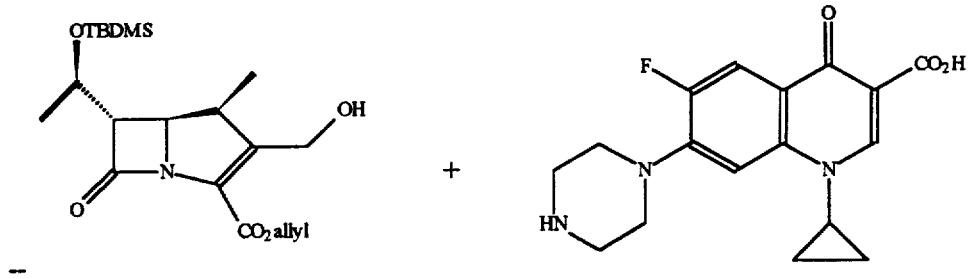
--.

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

23. Col. 34, second structure

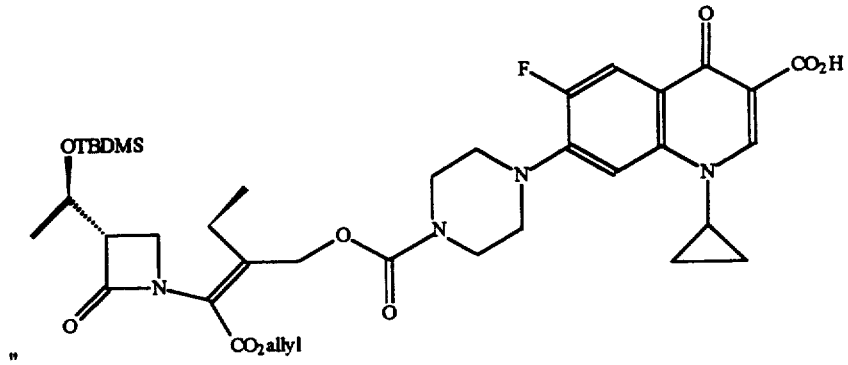

should read

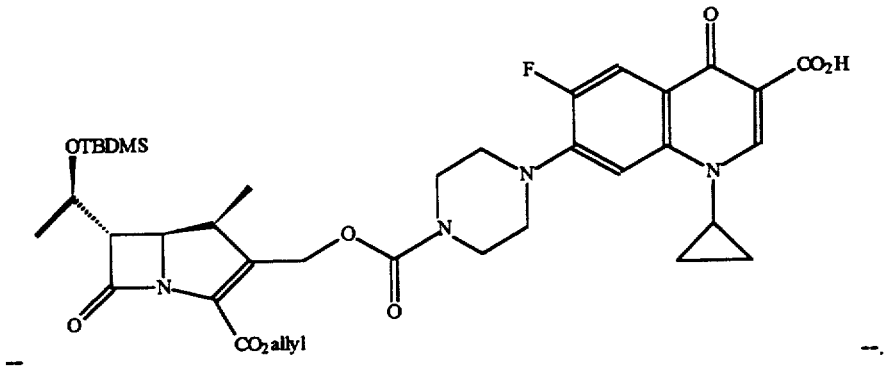

UNITED STATES PATENT AND TRADEMARK OFFICE
CERTIFICATE OF CORRECTION

PATENT NO. : 5,281,703

DATED : January 25, 1994

INVENTOR(S) : R. E. White and T. P. DeMuth, Jr.

It is certified that error appears in the above-identified patent and that said Letters Patent is hereby corrected as shown below:

24. Col. 34, third structure

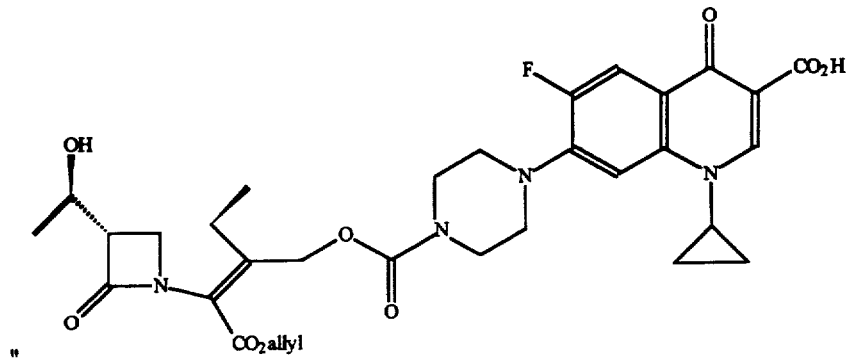

"

should read

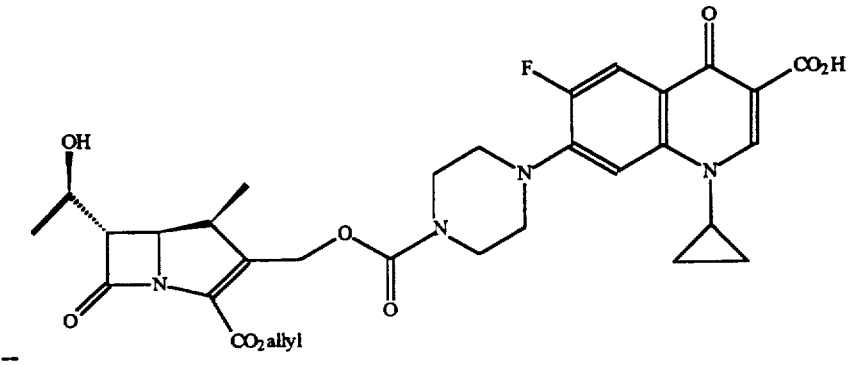

UNITED STATES PATENT AND TRADEMARK OFFICE
CERTIFICATE OF CORRECTION

PATENT NO. : 5,281,703
DATED : January 25, 1994
INVENTOR(S) : R. E. White and T. P. DeMuth, Jr.

It is certified that error appears in the above-identified patent and that said Letters Patent is hereby corrected as shown below:

25. Col. 35, first structure

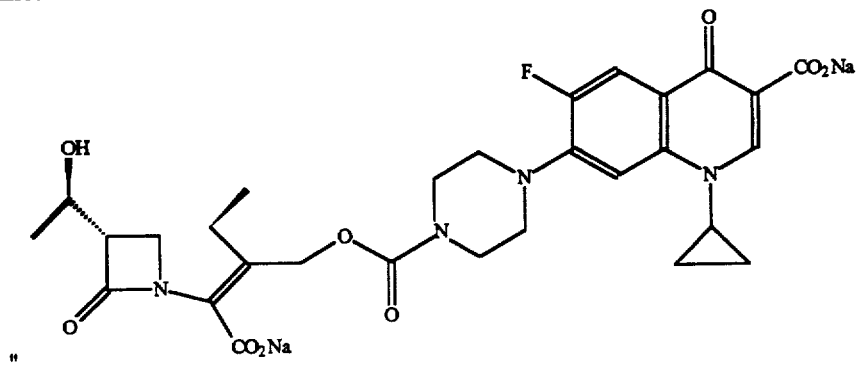

should read

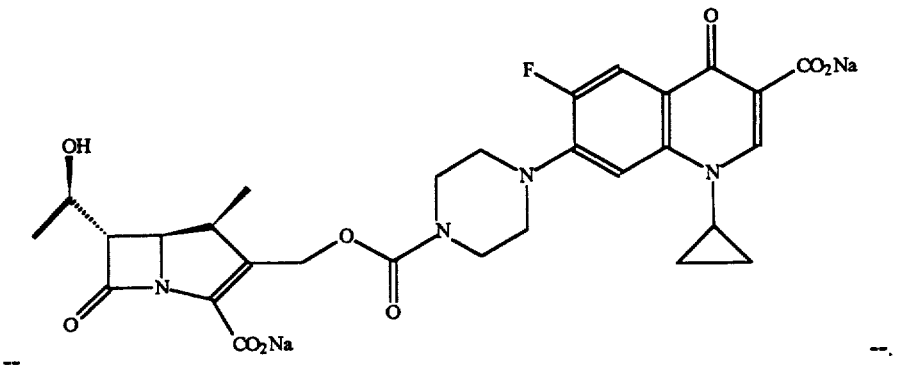

26. Col. 36, line 30 of Claim 1 of the patent, "is" should read --Q is--.